(12) United States Patent
Darvish

(10) Patent No.: US 11,865,165 B2
(45) Date of Patent: Jan. 9, 2024

(54) GNE AS A THERAPEUTIC AGENT

(71) Applicant: Daniel Darvish, Los Angeles, CA (US)

(72) Inventor: Daniel Darvish, Los Angeles, CA (US)

(*) Notice: Subject to any disclaimer, the term of this patent is extended or adjusted under 35 U.S.C. 154(b) by 150 days.

(21) Appl. No.: 16/574,644

(22) Filed: Sep. 18, 2019

(65) Prior Publication Data

US 2021/0100879 A1 Apr. 8, 2021

Related U.S. Application Data

(60) Provisional application No. 62/732,931, filed on Sep. 18, 2018.

(51) Int. Cl.

| | | |
|---|---|---|
| *A61K 38/47* | (2006.01) | |
| *A61K 9/00* | (2006.01) | |
| *A61K 38/45* | (2006.01) | |
| *A61K 45/06* | (2006.01) | |
| *A61P 21/04* | (2006.01) | |
| *C12N 7/00* | (2006.01) | |
| *C12N 9/12* | (2006.01) | |
| *C12N 9/24* | (2006.01) | |
| *C12N 15/86* | (2006.01) | |
| *A61K 31/713* | (2006.01) | |
| *A61K 38/52* | (2006.01) | |
| *A61P 3/00* | (2006.01) | |
| *A61P 21/00* | (2006.01) | |
| *A61K 48/00* | (2006.01) | |
| *A61K 38/17* | (2006.01) | |

(52) U.S. Cl.
CPC ............ *A61K 38/17* (2013.01); *A61K 9/0019* (2013.01); *A61K 38/45* (2013.01); *A61K 45/06* (2013.01); *A61P 21/04* (2018.01); *C12N 7/00* (2013.01); *C12N 9/1205* (2013.01); *C12N 9/2402* (2013.01); *C12N 15/86* (2013.01); *C12Y 207/0106* (2013.01); *C12Y 302/01183* (2015.07); *C12N 2750/14143* (2013.01)

(58) Field of Classification Search
CPC ..... A61K 48/005; A61P 21/00; C12N 15/861; C12Y 207/0106; C12Y 302/01183
See application file for complete search history.

(56) References Cited

FOREIGN PATENT DOCUMENTS

| | | |
|---|---|---|
| WO | 2012106465 A2 | 8/2012 |
| WO | 2013102904 A1 | 7/2013 |

OTHER PUBLICATIONS

Di Mattia et al. 2012; Structural insight into the unique properties of adeno-associated virus serotype 9. Journal of Virology. 86(12):6947-6958.*
Bell C.L., et al., "Identification of the Galactose Binding Domain of the Adeno-Associated Virus Serotype 9 Capsid," Journal of Virology, Jul. 2012, vol. 86, No. 13, pp. 7326-7333, Epub Apr. 18, 2012.
Chain A., Capsid protein VP1. PDB: 3UX1_A, Feb. 9, 2018. Retrieved on-line: <https://www.ncbi.nlm.nih.gov/protein/3UX1_A?report=genbank&log$=protalign&b last_rank=1&RID=TN627158013>, 4 pages.
Darvish, D., PCT/US 2020/050881, International Search Report, dated Nov. 26, 2020, 4 pages.
Darvish, D., PCT/US 2020/050881, Written Opinion, dated Nov. 26, 2020, 4 pages.

* cited by examiner

*Primary Examiner* — Suzanne M Noakes
*Assistant Examiner* — Jae W Lee
(74) *Attorney, Agent, or Firm* — Rahman LLC

(57) ABSTRACT

The invention relates to composition and methods for expressing UDP-GlcNAc 2-Epimerase/ManNAc Kinase enzyme (GNE) in a living organism. In preferred embodiments, the invention relates to treating disease condition that involves use of therapeutically effective amount of a composition described herein.

17 Claims, 8 Drawing Sheets

Specification includes a Sequence Listing.

Figure 3

```
  1 METYGYLQRESCFQGPHELYFKNLSKRNKQIMEKNGNNRKLRVCVATCNRADYSKLAPIMFGIKTEPEFFELDVVVLGSH  80
  1 --------------------------------MEKNGNNRKLRVCVATCNRADYSKLAPIMFGIKTEPEFFELDVVVLGSH  49
  1 -----------------MPIGDCSVAAKP--------RKQLLC-----------SLFQTTLGYRARASGWKPMVICRGSH  44
  1 --------------------------------MEKNGNNRKLRVCVATCNRADYSKLAPIMFGIKTEPEFFELDVVVLGSH  49
    --------------------------------------------------------------------------------

81 LIDDYGNTYRMIEQDDFDINTRLHTIVRGEDEAAMVESVGLALVKLPDVLNRLKPDIMIVHGDRFDALALATSAALMNIR 160
 50 LIDDYGNTYRMIEQDDFDINTRLHTIVRGEDEAAMVESVGLALVKLPDVLNRLKPDIMIVHGDRFDALALATSAALMNIR 129
 45 AFKDLINTYRMIEQDDFDINTRLHTIVRGEDEAAMVESVGLALVKLPDVLNRLKPDIMIVHGDRFDALALATSAALMNIR 124
 50 LIDDYGNTYRMIEQDDFDINTRLHTIVRGEDEAAMVESVGLALVKLPDVLNRLKPDIMIVHGDRFDALALATSAALMNIR 129
  1 ----------MIEQDDFDINTRLHTIVRGEDEAAMVESVGLALVKLPDVLNRLKPDIMIVHGDRFDALALATSAALMNIR  70

161 ILHIEGGEVSGTIDDSIRHAITKLAHYHVCCTRSAEQHLISMCEDHDRILLAGCPSYDKLLSAKNKDYMSIIRMWLGDDV 240
130 ILHIEGGEVSGTIDDSIRHAITKLAHYHVCCTRSAEQHLISMCEDHDRILLAGCPSYDKLLSAKNKDYMSIIRMWLGDDV 209
125 ILHIEGGEVSGTIDDSIRHAITKLAHYHVCCTRSAEQHLISMCEDHDRILLAGCPSYDKLLSAKNKDYMSIIRMWLGDDV 204
130 ILHIEGGEVSGTIDDSIRHAITKLAHYHVCCTRSAEQHLISMCEDHDRILLAGCPSYDKLLSAKNKDYMSIIRMWLGDDV 209
 71 ILHIEGGEVSGTIDDSIRHAITKLAHYHVCCTRSAEQHLISMCEDHDRILLAGCPSYDKLLSAKNKDYMSIIRMWLG--- 147

241 KSKDYIVALQHPVTTDIKHSIKMFELTLDALISFNKRTLVLFPNIDAGSKEMVRVMRKKGIEHHPNFRAVKHVPFDQFIQ 320
210 KSKDYIVALQHPVTTDIKHSIKMFELTLDALISFNKRTLVLFPNIDAGSKEMVRVMRKKGIEHHPNFRAVKHVPFDQFIQ 289
205 KSKDYIVALQHPVTTDIKHSIKMFELTLDALISFNKRTLVLFPNIDAGSKEMVRVMRKKGIEHHPNFRAVKHVPFDQFIQ 284
210 KSKDYIVALQHPVTTDIKHSIKMFELTLDALISFNKRTLVLFPNIDAGSKEMVRVMRKKGIEHHPNFRAVKHVPFDQFIQ 289
148 ------------------------------------SKEMVRVMRKKGIEHHPNFRAVKHVPFDQFIQ 179
                              [ ** GNE Allosteric domain ** ]
                              TLVLFPNIDAGSKEMVRVMRKKGIEHHPNFR
                                     Q   Q
                                     W   W
                                     L   L
                                     X   X 321 LVAHAGCMIGNSSCGVREVGAFGTPVINLGTRQIGRETGENVLHVRDADTQDKILQALHLQFGKQYPCSKIYGDGNAVPR 400
290 LVAHAGCMIGNSSCGVREVGAFGTPVINLGTRQIGRETGENVLHVRDADTQDKILQALHLQFGKQYPCSKIYGDGNAVPR 369
285 LVAHAGCMIGNSSCGVREVGAFGTPVINLGTRQIGRETGENVLHVRDADTQDKILQALHLQFGKQYPCSKIYGDGNAVPR 364
290 LVAHAGCMIGNSSCGVREVGAFGTPVINLGTRQIGRETGENVLHVRDADTQDKILQALHLQFGKQYPCSKIYGDGNAVPR 369
180 LVAHAGCMIGNSSCG

Figure 3 (cont'd)

```
401 ILKFLKSIDLQEPLQKKFCFPPVKENISQDIDHILETLSALAVDLGGTNLRVAIVSMKGEIVKKYTQFNPKTYEERINLI 480
370 ILKFLKSIDLQEPLQKKFCFPPVKENISQDIDHILETLSALAVDLGGTNLRVAIVSMKGEIVKKYTQFNPKTYEERINLI 449
365 ILKFLKSIDLQEPLQKKFCFPPVKENISQDIDHILETLSALAVDLGGTNLRVAIVSMKGEIVKKYTQFNPKTYEERINLI 444
370 ILKFLKSIDLQEPLQKKFCFPPVKENISQDIDHILETLSALAVDLGGTNLRVAIVSMKGEIVKKYTQFNPKTYEERINLI 449
260 ILKFLKSIDLQEPLQKKFCFPPVKENISQDIDHILETLSALAVDLGGTNLRVAIVSMKGEIVKKYTQFNPKTYEERINLI 339

481 LQMCVEAAAEAVKLNCRILGVGISTGGRVNPREGIVLHSTKLIQEWNSVDLRTPLSDTLHLPVWVDNDGNCAALAERKFG 560
450 LQMCVEAAAEAVKLNCRILGVGISTGGRVNPREGIVLHSTKLIQEWNSVDLRTPLSDTLHLPVWVDNDGNCAALAERKFG 529
445 LQMCVEAAAEAVKLNCRILGVGISTGGRVNPREGIVLHSTKLIQEWNSVDLRTPLSDTLHLPVWVDNDGNCAALAERKFG 524
450 LQMCVEAAAEAVKLNCRILGV------------------------------------------------------------ 470
340 LQMCVEAAAEAVKLNCRILGVGISTGGRVNPREGIVLHSTKLIQEWNSVDLRTPLSDTLHLPVWVDNDGNCAALAERKFG 419

561 QGKGLENFVTLITGTGIGGGIIHQHELIHGSSFCAAELGHLVVSLDGPDCSCGSHGCIEAYASGMALQREAKKLHDEDLL 640
530 QGKGLENFVTLITGTGIGGGIIHQHELIHGSSFCAAELGHLVVSLDGPDCSCGSHGCIEAYASGMALQREAKKLHDEDLL 609
525 QGKGLENFVTLITGTGIGGGIIHQHELIHGSSFCAAELGHLVVSLDGPDCSCGSHGCIEAYASGMALQREAKKLHDEDLL 604
471 ----------------GIGGGIIHQHELIHGSSFCAAELGHLVVSLDGPDCSCGSHGCIEAYASGMALQREAKKLHDEDLL 535
420 QGKGLENFVTLITGTGIGGGIIHQHELIHGSSFCAAELGHLVVSLDGPDCSCGSHGCIEAYASGMALQREAKKLHDEDLL 499

641 LVEGMSVPKDEAVGALHLIQAAKLGNAKAQSILRTAGTALGLGVVNILHTMNPSLVILSGVLASHYIHIVKDVIRQQALS 720
610 LVEGMSVPKDEAVGALHLIQAAKLGNAKAQSILRTAGTALGLGVVNILHTMNPSLVILSGVLASHYIHIVKDVIRQQALS 689
605 LVEGMSVPKDEAVGALHLIQAAKLGNAKAQSILRTAGTALGLGVVNILHTMNPSLVILSGVLASHYIHIVKDVIRQQALS 684
536 LVEGMSVPKDEAVGALHLIQAAKLGNAKAQSILRTAGTALGLGVVNILHTMNPSLVILSGVLASHYIHIVKDVIRQQALS 615
500 LVEGMSVPKDEAVGALHLIQAAKLGNAKAQSILRTAGTALGLGVVNILHTMNPSLVILSGVLASHYIHIVKDVIRQQALS 579

721 SVQDVDVVVSDLVDPALLGAASMVLDYTTRRIY 753 - NP_001121699
690 SVQDVDVVVSDLVDPALLGAASMVLDYTTRRIY 722 - NP_005467
685 SVQDVDVVVSDLVDPALLGAASMVLDYTTRRIY 717 - NP_001177317
616 SVQDVDVVVSDLVDPALLGAASMVLDYTTRRIY 648 - NP_001177312
580 SVQDVDVVVSDLVDPALLGAASMVLDYTTRRIY 612 - NP_001177313
```

Figure 7

| Grp | Sex | Beagle Real-Time PCR Cycle Crossing Point | | | | |
| --- | --- | --- | --- | --- | --- | --- |
| | | Tx Muscle | Non-Tx Muscle | Liver | Lung | Kidney |
| 1 | F | 0 | 0 | 0 | 0 | 0 |
| 2 | F | 23.59 | 0 | 0 | 22.8 | 0 |
| 1 | M | 0 | 0 | 0 | 0 | 0 |
| 2 | M | 24.13 | 0 | 24.18 | 23.75 | 0 |
| 2 | F | 22.31 | 0 | 23.82 | 0 | 0 |

… # GNE AS A THERAPEUTIC AGENT

FIELD OF THE INVENTION

The present invention is in the field of pharmaceutical therapeutics for diseases related to Sialic Acid biosynthesis, such as GNE Myopathy.

BACKGROUND OF THE DISCLOSURE

Hereditary Inclusion Body Myopathy (HIBM) is a young-adult onset progressive skeletal muscle wasting disorder, which causes severe physical incapacitation. There is currently no effective therapeutic treatment for HIBM. HIBM is an autosomal recessive disorder caused by mutation in the GNE gene. The GNE gene encodes for the bifunctional enzyme UDP-GlcNAc 2-epimerase/ManNAc kinase (GNE/MNK). This is the key rate-limiting enzyme catalyzing the first two reactions of cellular sialic production. Reduced sialic production consequently leads to decreased sialylation of a variety of glycoproteins, including critical muscle proteins such as alpha-dystroglycan (α-DG), neural cell adhesion molecule (NCAM), or neprilysin, or lead to altered expression of other genes such as gangliosides (e.g. GM3) synthase. This in turn leads to muscle degeneration. HIBM is also known as Distal Myopathy with Rimmed Vacuoles, Nonaka Myopathy, Vacuolar myopathy sparing the quadriceps, Inclusion Body Myopathy type 2 (IBM2 or HIBM2), or GNE myopathy.

SUMMARY OF THE INVENTION

Disclosed herein are methods of expressing UDP-GlcNAc 2-Epimerase/ManNAc Kinase enzyme (GNE) peptide in a cell of a subject compromising delivering into the cell of the subject nucleic acid or amino acid construct(s) that comprises a sequence encoding for a GNE peptide or a therapeutically active fragment thereof, wherein the sequence or sequences are described in the current invention, wherein upon delivering into the cell of the subject, the construct causes increase or altering cellular sialic content and/or concentration.

Also disclosed are methods of delivering the therapeutic product comprising: a) creating an intravenous access on a limb of a subject; b) applying a tourniquet or vascular occlusion at a point more proximal to the trunk of the subject than the intravenous access point; c) introducing a single or multiple dose of a therapeutic composition into the limb through the intravenous access, wherein the composition is of sufficient volume to increase intravascular pressure for extravasation of the composition; wherein, the composition comprises a polynucleotide molecule or protein (or peptide or polypeptide) molecule(s) encoding a GNE enzyme or a therapeutically active fragment thereof, wherein examples sequence(s) of such molecules are described in this invention herein.

Further, disclosed are methods of increasing sialic biosynthesis by delivering or producing a GNE peptide in a cell comprising transfecting the cell with a construct that comprises at least a nucleic acid or an amino acid sequence encoding one or more GNE peptide or a biologically active fragment thereof, wherein the GNE peptide has an amino acid sequence described herein.

BRIEF DESCRIPTION OF THE DRAWINGS

FIG. 3 shows the amino acid sequence of GNE isoforms and Allosteric domain including a visual representation corresponding to SEQ ID NOS: 3-17.

FIG. 7 shows quantitative real-time PCR results of drug vector presence in placebo control (group 1) and treated (group 2) animal subjects.

DETAILED DESCRIPTION OF THE EMBODIMENTS

Figure 1:
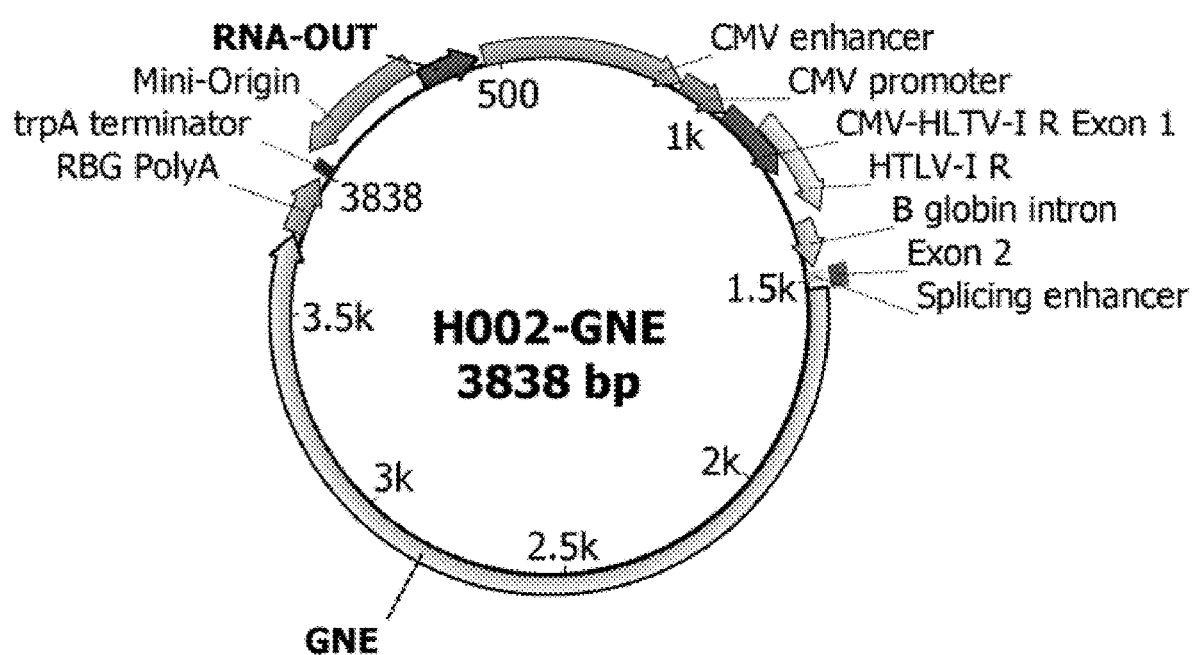
FIG. 1 shows a diagram of the H002-GNE expression vector described herein.

Disclosed herein are gene therapy methods and compositions for increasing production of sialic acid in a biological system by delivering the DNA coding region of the key enzyme of Sialic Acid biosynthesis (UDP-N-Acetylglucosamine 2-Epimerase/N-Acetylmannosamine Kinase, GNE). Disease conditions that will benefit from increased cellular sialic production, or enhanced GNE functions, include, but not limited to, GNE myopathy, Hereditary Inclusion Body Myopathy (HIBM) or Distal Myopathy with Rimmed Vacuoles (DMRV). The present methods and compositions also relate to reducing or eliminating non-human sialic acids (e.g. N-Glycolylneuraminate, Neu5Gc) from human cells or tissues. Non-human sialic acids may contribute to various human diseases, and long term reduction of cellular levels of non-human sialic acid may prove beneficial in preventing and treating those disease processes (WO/2010/030666) (Varki 2009). Increasing cellular production of Acetylneuraminate (Neu5Ac) can reduce cellular content of non-human sialic acids.

Being personally affected by HIBM, the inventor has developed and validated several gene therapy vectors through in-vitro studies over the years. Through many years of medical research, and evaluation of the data regarding various in-vivo delivery methods and vectors, an elegant and facile delivery method (route of administration, ROA) was chosen similar to a procedure known as the "Bier Block". Bier Block has been used safely in medical practice for over 100 years (dos Reis 2008). The ROA has been modified by the inventor using specific variations not previously described, with added advantages of improved transfection efficacy of the administered gene therapy composition.

As described below, the combination of the specific disease processes, the vectors, and (route of administration has numerous advantages over any others described to date. These advantages allow for facile translation to practical medical use (human subjects) and veterinary use (animal subjects). The vectors described herein can be used also for non-medical use in a biological organism.

Disclosed herein are the components of pharmacologic products and methods of delivering the pharmacologic products to the skeletal muscles or other organs (e.g. liver) of animals or human patient (e.g. patient affected with HIBM). The pharmacologic products can be a polynucleotide encoding the unmodified or modified forms of GNE protein, polypeptides or amino acid sequences and/or or recombinant proteins, polypeptides or amino acid sequences encoded by the unmodified or modified forms of GNE nucleotide. In some embodiments, the delivery methods include (1) external or internal occlusion of major vessels (arteries, veins, and/or lymphatic system) to achieve vascular isolation of the target organ systems, group of organs/tissues, or body area, and (2) administration of the therapeutic composition using vascular (e.g. intravenous) access. In some embodiments, the body organs/tissues/area that are isolated (target organs) are exposed to the composition being administered, while in other embodiments, the body organs/tissues/area are protected from exposure to the composition.

Description and Improvements of the Therapeutic Gene (GNE)

In some embodiments, the therapeutic products or compositions disclosed herein are polynucleotide (DNA) molecules, while in other embodiments, they are polypeptide (protein, protein fragments, amino acid sequences, peptide, polypeptide) molecules. In some embodiments, the polynucleotide molecule, either linear or circular, may contain various elements in addition to the coding sequence that encodes for the GNE protein, or a modified form of the GNE protein, or a therapeutic fragment peptide of either thereof, that is or becomes biologically active within a biological system. Such modified forms or fragment of GNE protein would retain significant similarity to the amino acid sequences described herein, or its biologically active domains or fragments, described for example in FIG. 3, or the disclosed sequences herein.

In some embodiments, the therapeutic methods disclosed herein are commonly known as "Gene Therapy", and comprise the administration of the above polynucleotide molecule. In other embodiments, the therapeutic methods disclosed herein are commonly known as "Enzyme Replacement Therapy (ERT)", and comprise the administration of the GNE protein, or a modified form of the GNE protein, or a fragment thereof, that is or becomes active within a biological system.

GNE gene encodes for the key enzyme of sialic acid production (UDP-N-Acetylglucosamine 2-epimerase/N-Acetylmannosamine Kinase, or GNE enzyme). Several disease conditions can benefit from increased expression of GNE. The most notable being the severely debilitating progressive muscle wasting disorder known as GNE myopathy, Hereditary Inclusion Body Myopathy (HIBM) or one of its distinct forms known as IBM2 or HIBM2, or Distal Myopathy with Rimmed Vacuoles (DMRV).

The GNE enzyme components or domains (e.g. series of 10 or more sequential amino acids) may be recombined to enhance desired functions of the GNE gene and reduce or eliminate undesired functions. For example, if production of high amounts of sialic acid (NeuAc) is desired in biological organisms, one may optimize the epimerase domain of the GNE gene to eliminate or reduce the allosteric inhibitory domain function. In organisms and animals having redundant ManNAc kinase activity, such as other enzymes able to efficiently perform phosphorylation of ManNAc, one may also reduce or eliminate the GNE kinase domain to reduce the size, the minimum effective dose, and/or maximize the maximum tolerable dose in a biological system.

Although the GNE enzyme, or various components or domains thereof, is also known to have cellular functions besides production of sialic acid (Hinderlich, Salama et al. 2004; Broccolini, Gliubizzi et al. 2005; Krause, Hinderlich et al. 2005; Salama, Hinderlich et al. 2005; Penner, Mantey et al. 2006; Wang, Sun et al. 2006; Amsili, Shlomai et al. 2007; Amsili, Zer et al. 2008; Kontou, Weidemann et al. 2008; Kontou, Weidemann et al. 2009; Paccalet, Coulombe et al. 2010), the hyposialylation of critical cellular molecules play an important role in human disease process (Huizing, Rakocevic et al. 2004; Noguchi, Keira et al. 2004; Saito, Tomimitsu et al. 2004; Tajima, Uyama et al. 2005; Ricci, Broccolini et al. 2006; Galeano, Klootwijk et al. 2007; Sparks, Rakocevic et al. 2007; Nemunaitis, Maples et al. 2010).

Oral Sialic Clinical Trials: Clinical phase 3 placebo controlled trial of oral medication using sialic acid extended release (aceneuramic acid extended-release, Ace-ER) at 6 g/day (2 g TID) was completed in 2017 (Clinicaltrials.gov protocol NCT02377921). The development of oral sialic acid treatment was terminated by sponsoring pharmaceutical company due to the lack of adequate proof of efficacy. It is believed that the lack of efficacy was caused by inability to deliver enough sialic acid to the skeletal muscles. Higher dose of 12 g/day in phase 2 trial resulted in higher gastrointestinal side effects without detectable improvement in efficacy (Clinicaltrials.gov protocol NCT01830972).

Oral ManNAc Clinical Trials: Clinical phase 2 open label trial of oral medication using N-Acetylmannosamine (ManNAc) at doses of 6 g/day (3 g BID) and 12 g/day (6 g BID) is currently underway in 2017-2018(Clinicaltrials.gov protocol NCT02346461). Results have not been released yet. It is believed by most skilled in the art that ManNAc oral dosing may not be much better than oral Ace-ER for increasing sialic content of skeletal muscles.

Thus, there is significant need for development of a pharmacologic product that is able to increase skeletal muscle sialic content more efficiently than oral dosing of sialic of ManNAc products.

Types of NeuAc and NeuGc Sialic: Increasing sialic acid and NeuAc/NeuGc ratio in biological systems is desired for several known reasons in human subjects. Mammals produce two different sialic molecules: (1) N-Acetylneuraminic acid (NANA or Neu5Ac), and (2) N-Glycolylneuraminic acid (Neu5Gc). CMP-NANA is converted to CMP-Neu5Gc by CMP-NANA hydroxylase (CMAH). Unlike other primates and mammals (including cow), humans are genetically deficient in Neu5Gc due to an Alu-mediated inactivating mutation of CMAH (Chou, Hayakawa et al. 2002). Thus, Neu5Ac is the only sialic acid produced by humans and many humans produce antibodies against Neu5Gc (Tangvoranuntakul, Gagneux et al. 2003). The NeuGc found in human tissues and cells are believed to be from food or cell culture media. Humans produce antibodies against NeuGc, potentially contributing to chronic inflammation, and various common disorders in which chronic inflammation is believed to be a significant factor (e.g. cancer, atherosclerosis, autoimmune disorders) (Hedlund, Padler-Karavani et al. 2008; Varki 2009). NeuGc can also promote human diseases, such as hemolytic uremic syndrome (HUS). A major cause of HUS is Shiga toxigenic *Escherichia coli* (STEC) infection. A highly toxic Shiga toxin subtilase cytotoxin (SubAB) prefers binding to glycan terminating in NeuGc (Lofling, Paton et al. 2009). This information increases our concern that NeuGc may also increase human susceptibility to some infectious agents.

Thus, it is desired to increase the content of NeuAc (human sialic acid) in food, and reduce the proportion of NeuGc found in meat and milk products. A potentially effective method to accomplish this is to increase GNE expression, and reduce or eliminate the CMAH expression in biological systems or organism used as either human or animal food (e.g. milk, meat, dairy, and other animal based products). CMAH may be reduced by either of genetic or metabolic technologies, including, but not limited to, genetic modification of animals to produce CMAH knock-out or knock-down animals, reduction of CMAH enzyme expression by polynucleotide technologies (expressed as inhibitory RNA or antisense oligonucleotide), or inhibition of CMAH enzyme by metabolic substrate analogues. NeuGc may also be reduced in biological systems by overexpression of the enzyme that converts NeuGc to NeuAc.

With few exceptions, plants do not typically produce sialic acid. GNE and other sialic acid pathway enzymes can be used in plant, vegetable, and fruit crops to increase sialic acid in food.

Modifications, additions, and/or removal of polynucleotide elements (e.g. promoters, enhancers, repeat elements) can be used to enhance expression in various tissues/organs or developmental stages, which may be desired in various fields of biotechnology including, but not limited to, pharmacologic, food, and cosmetic industries.

Figure 2:
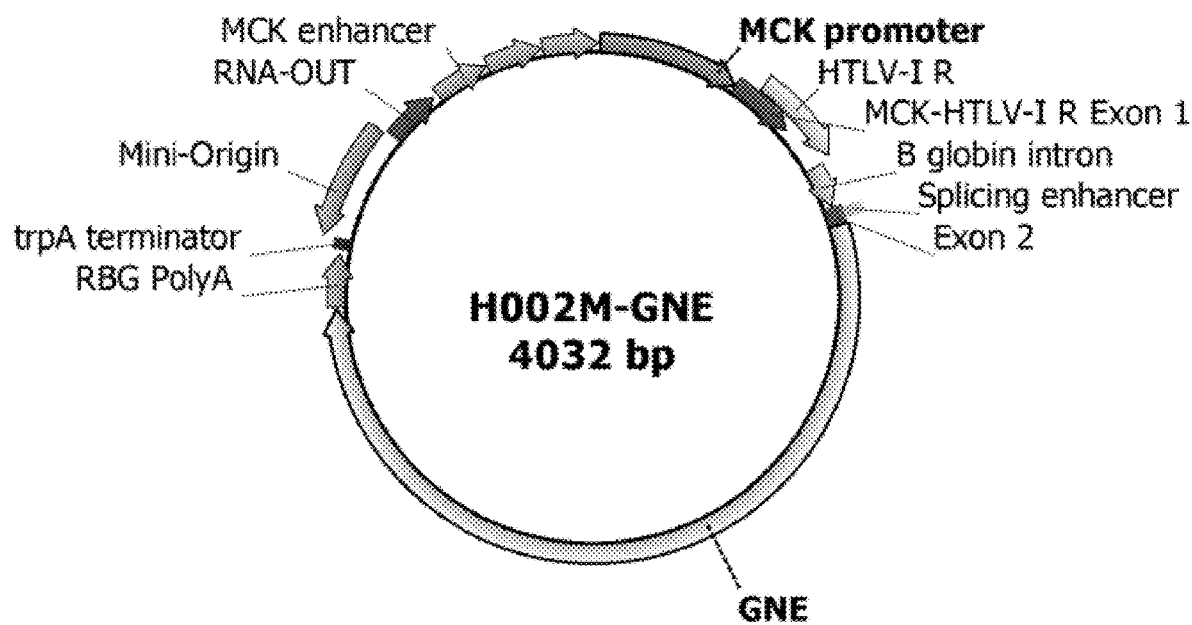
FIG. 2 shows a diagram of the H002M-GNE expression vector described herein.
Figure 4:
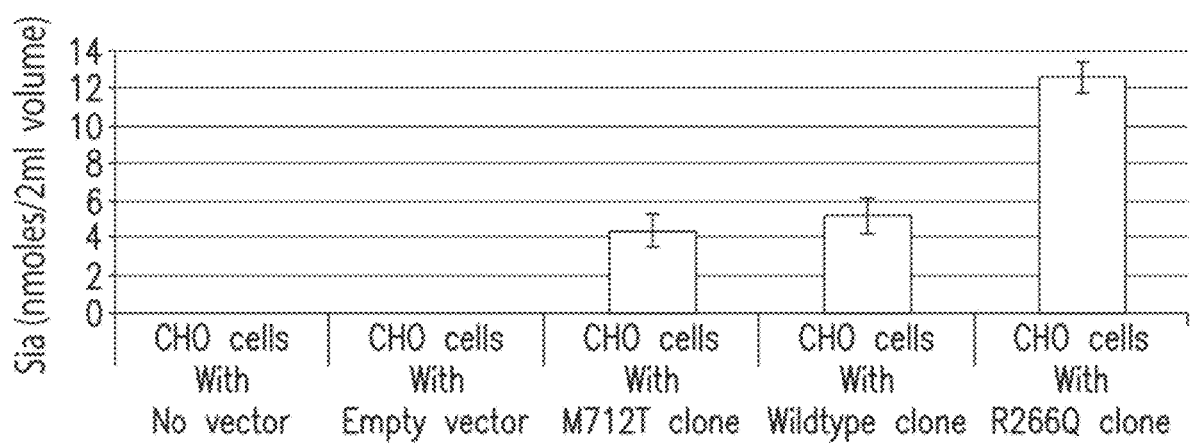
FIG. 4 shows the effect of Allosteric domain R266Q variation on Sialic Acid biosynthesis.

The expression vector elements disclosed are depicted in FIGS. 1 and 2. The disclosed vectors size and featured elements significantly improves in-vivo expression of the encoded GNE enzyme. The vectors comprise minimal prokaryotic or bacterial genome sequences. The vectors comprise either a chimeric CMV promoter that directs high mammalian cell expression (FIG. 1) or tissue specific promoter such as MCK (FIG. 2). The chimeric CMV promoter comprises a robust CMV promoter and start of exon 1, an HTLV-I R sequence which contains the 5' splice acceptor site, a synthetic 3' acceptor site based on the rabbit β globin intron, and an exon 2 splicing enhancer comprised of serine-arginine rich (SR) protein binding site (3 copies of GAAGAAGAC) to improve RNA export (Lavigueur et al. 1993). The vectors also comprise exon 2 kozak sequence upstream of the start codon for GNE. The use of the HTLV-I R region downstream of the CMV promoter increases the expression and the encoded protein in mice and nonhuman primates compared to CMV promoter based vectors (Barouch et al. 2005). Other elements include synthetic eukaryotic mRNA leader and polyA sequences are included in the vector, which further limits DNA sequence homology with the human or animal genome, which in-turn reduces the possibility of permanent integration in the host chromosome. The vectors also encode a consensus Kozak translation initiation sequence and ATG start codon. The vectors comprise antibiotic-free sucrose selection marker, which express a 150 bp antisense RNA (RNA-OUT) which knocks down the expression of a chromosomal counter-selectable marker (SacB) (Luke et al., 2009). SacB encodes a levansucrase, which is toxic in the presence of sucrose. Thus, plasmid selection is achieved in sucrose-containing media and enabling manufacturing and scale up of vector product without the use of use of antibiotics. Additionally, the vectors described comprise productive heat inducible Mini-origin replication that enables high yield manufacturing of vector produce, with fermentation yields up to 2.4 g/L of pDNA. The vectors elements and features are designed to be in compliance with US Food and Drug Administration (FDA) regulatory guidances regarding DNA Vaccine vector composition (FDA 2007).

Because skeletal muscle is an important tissue that is readily accessible and that is highly vascularized, it could be used as a factory to produce proteins with therapeutic values (reviewed in (Lu, Bou-Gharios et al. 2003; Ratanamart and Shaw 2006)). Indeed, it has been demonstrated that functional therapeutic proteins can be synthesized by the skeletal muscle and secreted into the blood circulation in sufficient amount to mitigate the pathology associated with disorders such as hemophilia, Pompe disease, Fabry's disease, anemia, emphysema, and familial hypercholesterolemia. The ability to express recombinant proteins in skeletal muscle is also an important issue for the treatment of neuromuscular disorders such as Duchenne and limb girdle muscular dystrophy. These disorders are caused by mutations of a gene that produces an essential muscle protein. One potential treatment for such disorders is gene transfer, whose objective is to introduce into the muscle a normal and functional copy of the gene that is mutated.

Thus, in one aspect, disclosed herein are methods to utilize muscle as protein factory to over-produce and secrete sialic acid. In some embodiments, the methods disclosed herein result in an increase of Neu5Ac biosynthesis in plasma, and the reduction of Neu5Gc concentration from cells.

Description and Improvement of the Therapeutic Product

In some embodiments, the therapeutic product is a polynucleotide, while in other embodiments, the therapeutic product is a polypeptide. In some embodiments, the polynucleotide is a DNA molecule, which can comprise the full-length coding region for a protein, the coding region for a domain of a protein, or a coding region for a protein fragment, which is shorter than a recognized and identified domain of a protein. Thus, the polynucleotides disclosed herein can range from oligomers of at least 15 base pairs in length to DNA molecule comprising the full-length coding region for a protein.

In some embodiments, the polypeptide is a full-length protein, e.g., an enzyme or a receptor, while in other embodiments, the polypeptide is a protein fragment. In some embodiments, the protein fragment corresponds to a recognized and identified domain of a full-length protein, while in other embodiments, the polypeptide is shorter than a recognized and identified domain of a protein. Thus, the polypeptides disclosed herein can range from oligomers of at least 5 amino acids in length to full-length proteins. In some embodiments, the protein fragment is a therapeutically active protein fragment. By "therapeutically active protein fragment" it is meant that the protein fragment under physiological conditions has the same biochemical activity (e.g. catalyzes the same reaction or reactions) as the wild-type GNE protein, although it may perform the function at a different rate.

In some embodiments, the polynucleotide is a linear DNA molecule whereas in other embodiments, the polynucleotide is a circular DNA molecule.

In some embodiments, the polynucleotide is a circular DNA (plasmid, mini-plasmid, minicircle) able to express the GNE gene in the desired biological system. The vectors described in this application have few benefits, which include reduced size, reduced bacterial sequence content, antibiotic free selection, and improved cellular transduction and expression. Other similar vectors known to those of skill in the art can also be used with the methods described herein.

In some embodiments, the polynucleotide therapeutic product, whether linear or circular, is administered as naked DNA, combined with other molecules to produce various cationic or anionic particles, or co-administered with other pharmacological agents (e.g. excipients, vasodilators, analgesics, etc,) to maximize efficacy of therapy and minimize patient discomfort. Instead of a polynucleotide, other pharmacologic products may be administered using the stated delivery or ROA.

Unlike in vitro studies, where net positive zeta potential is a more efficient cellular entry of a polynucleotide, in vivo transduction of skeletal muscle seems to be more efficient using a polynucleotide having a net negative charge (PCT WO/2004/062368).

In one embodiment, muscle specific promoters may be used to reduce chance of host immune response against the transgene and enhance the duration of intramuscular expression of the transgene. The backbone plasmid elements can be altered to allow for muscle specific expression. The ability to achieve high-level and long-term recombinant protein expression after gene transfer in skeletal muscle is desired in many disease conditions. This can be achieved using promoters and enhancers specific for muscle.

Several different muscle specific promoters have been described to date. The muscle creatine kinase (MCK) promoter and truncated versions are the most common muscle specific promoters used (Hauser, Robinson et al. 2000; Yuasa, Sakamoto et al. 2002; Sun, Zhang et al. 2005; Sebestyen, Hegge et al. 2007; Wang, Li et al. 2008). The synthetic C5-12 promoter and similar promoters show promise of being muscle specific while driving high expression of transgene (Li, Eastman et al. 1999). This C5-12 promoter drives expression levels similar to the ubiquitous CMV promoters in AAV vectors (Gonin, Arandel et al. 2005). The C5-12 can be further improved by adding the MCK enhancer (E-Syn promoter) (Wang, Li et al. 2008). The hybrid-myosin heavy chain enhancer-/MCK enhancer-promoter (MHCK7) promoter also was used for high expression in muscles (Salva, Himeda et al. 2007). The desmin promoter is also recently described as a muscle-specific promoter capable or driving high level expression in muscle cells (Pacak, Sakai et al. 2008; Talbot, Waddington et al. 2010). The upstream enhancer elements (USE, USEx3/AUSEx3) of genes such as the troponin gene is also a promising candidate for developing muscle specific promoters (WO 2008124934 20081023; B lain, Zeng et al. 2010).

As disclosed herein, the GNE-encoding sequences, and/or the associated delivery vehicles used therewith, may be targeted towards specific cell types, for example, muscle cells, muscle tissue, and the like. For example, the promoter associated with the GNE coding sequence can be made to express GNE only in specific tissues or developmental stages. Alternatively, the expression cassette can be packaged with other molecules, compounds, or biologic moieties (e.g. protein/carbohydrate/lipid containing molecules, part or whole antibody molecules, part or whole cytokine molecules, viral capsids) to generate a biological mixture or specific biological particles designed to bind to and enter specific cell types. This binding or affinity can facilitate the uptake of the DNA into the cell. For delivery into muscle, in particular, anionic (with negative net molecular charge or zeta potential, in the pH relevant to the final composition, ROA, or subject living organism), non-liposomal, DNA containing particles are well-suited. However, cationic (with positive net molecular charge or zeta potential, in the pH relevant to the final composition, ROA, or subject living organism), liposomal, as well as other DNA containing biological mixtures or particles, are also suited for uptake into myopathic muscle with compromised cell wall. In some embodiments, these protein, carbohydrate, and/or lipid containing molecules targeting moieties are, but are not limited to, microbial, plant, microbial, or synthetic compounds (e.g. antibodies, cytokines, lectins, other large or small molecules). Therefore, the GNE nucleic acid translation can be limited to the target tissue or organ in need of increased GNE activity or sialic acid. Either an anionic or cationic particle may show a more favorable efficacy and safety/toxicity profile depending on target tissue(s), disease condition(s), and desired therapeutic outcome(s).

In some embodiments, polynucleotides products described herein comprise the following elements: 1) Bacterial Control Elements, which are active in bacteria for the purpose of selection and growth process, 2) Eukaryotic Control Elements, which are active in eukaryotic or mammalian cells for the purpose of expression of a therapeutic gene product or recombinant protein, and 3) the GNE coding region, which is the therapeutic gene product or recombinant gene. In some embodiments, prokaryotic/bacterial selection marker is based on antibiotic resistance (e.g. kanamycin resistance), or non-antibiotic or antibiotic-free (e.g. RNA-OUT, present in the vectors disclosed herein). In other embodiments, other elements are used for efficient plasmid production (e.g. mini-origin depicted in the vectors disclosed herein). In additional embodiments, eukaryotic promoter, enhancer, introns or other elements are used for efficient transcription and translation of the therapeutic protein, peptide, or polypeptide encoded by the vector.

To minimize potential spread of antibiotic resistance, prokaryotic selection marker that is not based on antibiotic resistance is preferred by regulatory agencies such as World Health Organization (WHO), US Food and Drug Administration (FDA), or European Agency for the Evaluation of Medicinal Products (EMEA) (Williams, Carnes et al. 2009).

Rationale for using plasmid DNA: Clinical use of naked or plasmid DNA (pDNA) to express therapeutic genes is a promising approach to treat muscle disease caused by GNE myopathy or HIBM or IBM2. Naked DNA as gene therapy vehicle has an excellent safety record and repeat administration in the same subject can achieve higher expression levels. (Hagstrom, Hegge et al. 2004; Wolff, Lewis et al. 2005; Wolff, Budker et al. 2005; Herweijer and Wolff 2007; Braun 2008; Duan 2008; Zhang, Wooddell et al. 2009) Depending on ROA, pDNA delivered to skeletal muscle of rodents or primates is retained in myofibers and expresses the encoded gene product for many months (Danko, Fritz et al. 1993; Danko, Williams et al. 1997; Sebestyen, Hegge et al. 2007). Unlike Adeno-Associated Virus (AAV) and other viral vectors which can induce cellular or humoral immunity (Yuasa, Yoshimura et al. 2007; Mingozzi, Meulenberg et al. 2009), pDNA does not typically elicit an immune response against the vector (Hagstrom, Hegge et al. 2004; Romero, Braun et al. 2004; Glover, Lipps et al. 2005; Wolff, Budker et al. 2005), which makes it possible to repeat administrations in same subject. Additionally, compared to viral or based vectors, pDNA is relatively inexpensive to produce in large quantities and remains stable for many months (Walther, Stein et al. 2003; Urthaler, Ascher et al. 2007; Voss 2007).

Route of Administration (ROA). Description and Improvement of Delivery

The preferred embodiments of the delivery ROA (Hydrodynamic Infusion or Hydrodynamic Limb Vein, HLV infusion) comprises external or internal occlusion of major vessels (arteries, veins, and/or lymphatic system) followed by rapid intravascular (intravenous or intra-arterial) infusion of a medicament fluid. In one embodiment of Hydrodynamic Infusion, an external tourniquet is placed on the limb of a human or animal subject, and the therapeutic product is administered using a peripheral intravenous access using a specific volume (typically 30-50% of the limb volume below or distal to the tourniquet) in a specific amount of time or volume flow (typically 1-5 ml/second). This is similar to commonly used medical procedures known as "Intravenous Regional Anesthesia" or "Bier Block", which has been used safely and effectively for more than a century to reduce the exposure to internal vital organs, reduce the needed effective dose, and/or maximize the desired effect/dose of pharmacologic compounds such anesthetics, antibiotics, or chemotherapy agents. Bier Block has been used to induce intravenous regional anesthesia (eliminating the need for general anesthesia) in arm or hand surgery (dos Reis 2008; Vlassakov and Bhavani 2010). Similar method is used in oncology by the name of "Isolated Limb Infusion" or "Isolated Limb Perfusion" for the administration of chemotherapeutic compounds to a specific limb, allowing for reduction in dose and exposure to internal organs (Kroon and Thompson 2009). Placing a tourniquet on limbs has also been used effectively for many centuries to reduce bleeding following severe trauma, or to reduce exposure of internal organs to toxins following exposure (e.g. venomous snake and other animal bites).

When administering gene therapy or biologics using the same or very similar delivery, the delivery method is described in medical literature by multiple names, including "hydrodynamic", "transvenular", "transvenous", "transvascular", "vascular", "retrograde", "limb vein", "peripheral vein", "intravenous", "intravascular", "retrograde", "extravasation", "high pressure", "pressurized", "isolated limb", "vascular isolation", "vascular occlusion", "blood flow occlusion", or any combination thereof (Su, Gopal et al. 2005; Sebestyen, Hegge et al. 2007; Vigen, Hegge et al. 2007; Zhang, Wooddell et al. 2009; Haurigot, Mingozzi et al. 2010; Hegge, Wooddell et al. 2010; Powers, Fan et al. 2010). Despite specific concerns, post-phlebitic syndrome or post-procedure angiopathy has not been noted following performance of vascular occlusion procedures following canine (dog) studies (Haurigot, Mingozzi et al. 2010).

In some embodiments, disclosed herein, the delivery method has been improved. Human and animal limbs of same volume may be composed of varying ratios of muscle and non-muscle (e.g. fatty or scar) tissues. Muscle is often more vascular and requires higher blood flow than lipid or scar tissue. Thus, administering therapeutic products using a specific volume may not confer optimum distribution of the therapeutic product in limbs of individuals. Limbs with higher muscle/non-muscle tissue may require higher infusion volumes to achieve same therapeutic benefit. Controlling the infusion based on intravascular (or infusion line) pressure and duration of infusion may convey improved distribution of therapeutic product to the target limb. Based on the current invention, the following modifications improves this ROA by "Hydrodynamic Infusion" described herein in a way that is not obvious, more efficacious, more practical, and reasonably safe for clinical use in a human subject:

1) Placing the tourniquet of specific pressure at 325-450 mmHg for a human patient. This pressure range is considered excessive by one skilled in the art, and most practice pressures slightly higher than systolic blood pressure ranging from 140-325 mmHg for similar procedures.

2) For effective retrograde extravasation of the infused fluid composition, the intravenous access site should be at a distal vein around the wrist or dorsal side of hand for a human arm, and/or around the ankle or dorsal side of the foot for a human leg.

3) Rapid increase of infusion fluid flow to achieve a specific intravascular (or infusion line) pressure typically below the tourniquet pressure (e.g. if tourniquet pressure is maintained at 320 mmHg, the infusion line intraluminal pressure maintained at 300-320 mmHg). These pressures are not considered by one skilled in the art due to relatively significant safety concerns. Recent publications consider infusion line pressures not exceeding 300 mmHg (Fan, et, al, 2015).

4) Effective extravasation is achieved by maintaining the infusion line pressure by controlling infusion fluid flow rate and/or flow pressure. This is not obvious to one skilled in the art as previous publications show that one skilled in the art considers adding vasodilators or vasodilators (such as papaverine or histamine) or other drug added to the pharmacologic composition to achieve more effective extravasation of the composition (Gruntman, et, al, 2015).

5) Maintaining the infusion line pressure for a specific duration of time (5-10 minutes for a human arm and 12-20 minutes for a human leg). Maintaining a shorter or longer duration does not significantly alter effectiveness of the ROA, and may unnecessarily increase chance of clinically adverse effects. This is not obvious to one skilled in the art since based on prior clinical experience, and as evident by recent relevant publications (Fan, et. al., 2015), an artisans would likely choose longer duration of vascular occlusion and lower pressures proposed.

6). Using a specifically designed device to safely achieve parameters described above in 1 and 2. Such device may automatically control the flow rate and pressure of the infusion line based on the set tourniquet pressure. For safety, such device would automatically stop infusion (flow rate of zero mL/sec) upon detection of parameters such as sudden drop in infusion line pressure, air bubble within the infusion line, or fluid level within the container holding the fluid to be infused.

By selecting the site of vascular administration distal or proximal to the site of vascular occlusion, one can either expose or protect the target organs, tissues, or body area.

Rationale for using ROA "Hydrodynamic Infusion" delivery: Although commonly used for DNA vaccination trials, pDNA delivered by intramuscular (IM) approach is inefficient for muscle diseases demanding delivery of therapeutic product to an entire limb or the whole body (Jiao, Williams et al. 1992). Intravenous (IV) plasmid is cleared rapidly by the liver (Liu, Shollenberger et al. 2007). However, combined with the ROA that is similar to Bier Block, hydrodynamic limb vein (HLV), or Isolated Limb Infusion delivery, the pDNA administered intravenously (IV) to a distal limb vein as described above, can effectively and uniformly transfect skeletal muscle of an entire limb in small and large animals including non-human primates (Hagstrom, Hegge et al. 2004). This ROA by Hydrodynamic Infusion as described herein is likely to cause reversible microvasculature damage (Toumi, Hegge et al. 2006; Vigen, Hegge et al. 2007). A single dose can result in long-term gene expression, and the ease of repeat administration makes the ROA by Hydrodynamic Infusion suitable for delivering GNE transgene to the limbs of a human patient. Using a tourniquet, the blood flow in an arm or leg is temporarily occluded, and a plasmid DNA solution is rapidly injected intravenously. This elevates the pressure within the occluded region, leading to remarkably efficient migration (or extravasation) of the gene vehicle into the adjoining myofibers. Blood flow is restored to normal in 5-20 minutes, with no irreversible or persistent adverse effect. Similar high pressure intravenous approaches are being adopted and adapted for delivery of DNA, and possibly other potential therapeutic molecules, to various organs. (Al-Dosari, Knapp et al. 2005; Arruda, Stedman et al. 2005; Wolff, Lewis et al. 2005; Herweijer and Wolff 2007; Toromanoff, Cherel et al. 2008, Powers et al. 2010, Fan et al. 2015).

GNE myopathy or HIBM is an example of an ideal orphan disorder to be treated by the drug product comprising the disclosed expression vectors using the described ROA by Hydrodynamic Infusion for the following reasons:

Low GNE expression may be therapeutic: GNE gene is relatively small, functioning as a protein enzyme that is expressed at low levels in skeletal muscle. Expression of low amounts of wild-type, or very low amounts of sialuria form of GNE, may prove remarkably effective or even curative. Additionally, it is possible to use a hypermorphic form of the GNE gene allowing for relatively low expressions of the GNE to translate to significant therapeutic benefit. This is in sharp contrast to other muscle diseases such as Duchenne' or Becker muscular dystrophies where relatively large amounts of dystrophin (or truncated mini-dystrophin) are needed to realize a functionally meaningful therapeutic benefit. Furthermore, the use of hyperactive or hypermorphic GNE, or a pharmaceutically acceptable salt thereof, or a pharmaceutical composition containing either entity, for the manufacturing of a medicament would be remarkably effective and safe for the treatment of subjects in need of such treatment. Such hypermorphic GNE may be in the form of polynucleotide (e.g. DNA) or polypeptide (e.g. protein enzyme).

Treating limbs alone may be sufficient and meaningful therapy: GNE myopathy initially affects the distal muscles of arms and legs. Trunk muscles are clinically affected later in disease course. Vital organs, including heart and lungs, are not clinically affected in majority of patients. By halting the muscle degeneration thereby stabilizing the arm and leg function, the patients (human subjected suffering from GNE myopathy) would benefit from improvement quality of life and meaningful delay of loss of their independence. The patients would be able to stay active and independent longer.

Host immune response to the transgene is unlikely: Over 99% of known patients express GNE protein that differs from wild-type by one amino acid (missense mutation). Additionally, GNE is an evolutionarily conserved enzyme with 98% homology between mice and men at the amino acid level. Thus, the chance of host immune response or producing neutralizing antibodies against the GNE transgene is minimal. Coupling GNE with a muscle specific promoter such as creatine kinase (CK) further reduces chance of host antibody response (Fabre, Bigey et al. 2006). Additionally, the ROA of Hydrodynamic Infusion further reduces chance of undesirable host immune response (Toromanoff et. al. 2010).

Potential for beneficial bystander or distant effects: Unlike dystrophinopathies, where expression of dystrophin (large structural protein) within a myofiber seems to benefit only the site of injection, in GNE myopathy it is likely that Neu5Ac (small molecule, 9 carbon sugar) will not remain within a limited or confined region of the myofiber. Neu5Ac produced by one myofiber will likely benefit neighboring myofibers. Following data further support this hypothesis: (a) Sia deficient mouse models are able to use Neu5Ac present in serum (Malicdan, Noguchi et al. 2009) (b) hyposialylated cells became re-sialylated after their growth medium was supplemented with ManNAc (Schwarzkopf, Knobeloch et al. 2002) and (c) adding 5 mM ManNAc or Neu5Ac, but not GlcNAc, to the media restored the sialic acid content of primary DMRV (or GNE myopathy) fibroblasts or myotubes from 60-75% of control to normal levels (Noguchi, Keira et al. 2004). Bystander effect, and possibility of distant effect, was observed in a single patient trial (Nemunaitis, Maples et al. 2010). The patient received GNE-lipoplex intramuscular injection of forearm (Extensor Carpi Radialis Longus, ECRL). Transient increase in strength, recombinant GNE (rGNE) expression, and increase of cell surface sialic acid was observed at the injection site and adjacent compartment muscles. Possibility of distant effect was also suggested following the surprising observation that distant muscle groups (trapezius and quadriceps) improved transiently in correlation with left ECRL rGNE transgene expression and increased sialylation (Nemunaitis, Maples et al. 2010).

Safety/Toxicology

Based on available information, the disclosed vectors herein are expected to be a safe and effective for use in GNE myopathy patients. Generally, negatively charged (negative zeta potential) plasmid DNA vectors as a gene therapy vehicle has an excellent safety record. Unlike most viral vectors such as AAV, repeat administration of plasmid DNA vectors delivered by Hydrodynamic Infusion ROA to the same subject can achieve higher expression levels (Hagstrom, Hegge et al. 2004; Wolff, Lewis et al. 2005; Wolff, Budker et al. 2005; Herweijer and Wolff 2007; Braun 2008; Duan 2008; Zhang, Wooddell et al. 2009).

Safety of GNE plasmid: Rodent toxicology studies using GNE-plasmid are currently underway. Preliminary data suggests naked plasmid will prove much safer than GNE-lipoplex that has already been administered to a human patient (Phadke, Jay et al. 2009; Nemunaitis, Maples et al. 2010). We conducted a recent pre-GLP toxicology study of 14 day duration on 12 mice (strain B6; FBV mixed inbred, 6 male and 6 female of age 4-10 months). Male and female mice were divided equally and randomly into experiment and control groups. The experiment group received high dose GNE plasmid (0.6 mg suspended in 0.1 ml normal saline) administered via IV tail, and the control group received only 0.1 ml normal saline. The groups were further divided into 3 dose frequency groups of 2 mice (1 female, 1 male) each as follows: 1) every day administration for 14 days, 2) every other day administration, and 3) once per week. All animals survived the experiment. No significant change were observed between the experiment and the control groups with respect to all measured parameters, which included body weights, temperature, food and water intake, CBC blood tests (performed at pre-dose day 1 and at necropsy on day 15). No significant change in the gross pathology was observed between the experiment and the control groups with respect to 12 organs, including brain, lung, heart, liver, kidney, spleen, stomach, intestines, bladder, genitals, lymph nodes, and muscle. The daily human equivalent dose (HED) was 120 mg, and the maximum 14 day total HED was 1440 mg.

Safety of the disclosed GNE expression vectors: In comparison to naked plasmid GNE vectors (bearing a net negative zeta potential), the GNE-lipoplex form is far more toxic. To produce the lipoplex, the plasmid vector was encapsulated in a cationic liposome (bearing a net positive zeta potential) composed of 1,2-dioleoyl-3-trimethylammonium-propane (DOTAP) and cholesterol (GNE-lipoplex). It is generally believed by one skilled in the art, that a relatively strong net positive zeta potential on lipoplex particles are required for effective cell transduction (Takeuch et. al. 1996). The vector was injected into BALB/c mice, and single intravenous (IV) infusion of GNE-lipoplex was lethal in 33% of animals at 100 g (0.1 mg) dose, with a small proportion of animals in the 40 g cohort demonstrating transient toxicity (Phadke, Jay et al. 2009). Based on a poster presented at 2010 ASGCT conference (Phadke, Jay et al. 2010), the maximum tolerated dose for administration of multiple injections of GNE-lipoplex in Balb/c mice was (1) 20 g per injection (Human equivalent dose (HED)=5.2 mg), or (2) a cumulative dose of 80 g (HED=20.8 mg). In the ongoing dose escalation trial, the patient has received several infusions (0.4, 0.4, 1.0 mg) of 1-3 months apart, and transient grade 1, 2 tachycardia and fever were observed within 12 hours of each infusion. Patient's liver function tests were also reported as transiently elevated, but exact numbers were not reported in the abstract (Nemunaitis, Jay et al. 2010).

Safety of Route of Administration (ROA) by Hydrodynamic Infusion: Potential side effects of the hydrodynamic delivery methods have been studied in non-human primates at double the tourniquet pressures proposed for the current study. The procedure was determined to be safe, without any non-reversible or long-lasting side effects (Vigen, Hegge et al. 2007; Hegge, Wooddell et al. 2010). The ROA procedure is similar to the Bier Block used for regional anesthesia and surgical homeostasis that has been used safely and effectively for over a century. The main difference is that in ROA Hydrodynamic Infusion, exsanguination is unnecessary, and duration of the procedure is typically 15 minutes in Hydrodynamic Limb Vein (HLV) infusion (Hegge, Wooddell et al. 2010). Histologic studies in non-human primates have shown that the HLV procedure caused transient muscle edema but no significant muscle damage (Hagstrom, Hegge et al. 2004; Toumi, Hegge et al. 2006). T2-weighted MRI images in non-human primates also showed that the procedure caused transient muscle edema but there was no persistent muscle derangement such as a compartment syndrome (Vigen, Hegge et al. 2007). Magnetic resonance angiography in nonhuman primates revealed vascular effects consistent with a transient effect on capillary permeability but no long-term abnormalities of concern (Vigen et al., 2007). These initial studies were performed using much higher tourniquet pressures (700 mmHg) than we are describing in the current invention herein. Also, the injection volume of 45-50% of the limb volume was used in these studies, and we are modifying the injection/limb volume to below 40% for a human subject. Additionally, the expression vectors described herein will enter myopathic fibers more effectively than normal muscle due to reduced integrity of the muscle cell walls, thus justifying the reduced pressures and injection volumes.

In summary, the HLV delivery method using pDNA is considered mature technology that has proven effective and safe in non-human primates, and is ready to be tested in clinical therapeutic trials (Wells 2004; Al-Dosari, Knapp et al. 2005; Herweijer and Wolff 2007). Using a similar administration procedure, a volume escalation study in adult patients suffering from muscular dystrophy is underway at University of North Carolina, Chapel Hill (Powers, Fan et al. 2010, Fan et. al. 2015). The main disadvantage of this approach is the inability to easily transfect diaphragm, heart, and trunk/neck muscles without invasive methods to temporarily clamp the major internal vessels (e.g. surgical, laparoscopic, or transcutaneous balloon-occlusion). Although this disadvantage is significant for many muscular dystrophies, it is not nearly as important in patients affected by GNE myopathy or HIBM. Many HIBM patients live into their senior years, and their heart and lungs have not been reported to become clinically affected as severely as other muscle wasting diseases such as Duchenne Muscular Dystrophy. Thus, HLV delivery of the expression vectors described herein for delivering GNE transgene to limb skeletal muscles is an attractive therapeutic option for GNE myopathy that may delay the loss of physical independence, and offer significant hope for many patients.

The GNE-encoding sequences and related compositions may contain any conventional non-toxic pharmaceutically-acceptable carriers, adjuvants or vehicles. In some embodiments of the invention, the pH of the formulation may be adjusted with pharmaceutically acceptable acids, bases or buffers to enhance the stability of the formulated composition or its delivery form. For example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U. S. P. and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid may be used in the preparation of injectables.

According to certain embodiments, a Plasma-Lyte® carrier may be employed and used to deliver a GNE-encoding sequence, particularly for parenteral injection. (Baxter Laboratories, Inc., Morton Grove, Illinois). Plasma-Lyte® is a sterile, non-pyrogenic isotonic solution that may be used for intravenous administration. Each 100 mL volume contains 526 mg of Sodium Chloride, USP (NaCI); 502 mg of Sodium Gluconate (C6H11NaO7); 368 mg of Sodium Acetate Trihydrate, USP (C2H3NaO2^H2O); 37 mg of Potassium Chloride, USP (KCI); and 30 mg of Magnesium Chloride, USP (MgCl2»6H2O). It contains no antimicrobial agents. The pH is preferably adjusted with sodium hydroxide to about 7.4 (6.5 to 8.0).

The injectable formulations used to deliver the current inventions expression vectors may be sterilized, for example, by filtration through a bacterial-retaining filter, or by incorporating sterilizing agents in the form of sterile solid compositions, which can be dissolved or dispersed in sterile water, Plasma-Lyte® or other sterile injectable medium prior to use.

In order to prolong the expression of a therapeutic GNE enzyme within a system (or to prolong the effect thereof), it may be desirable to slow the absorption of the composition from subcutaneous or intramuscular injection. This may be accomplished by the use of a liquid suspension of crystalline or amorphous material with poor water solubility. The rate of absorption of the composition may then depend upon its rate of dissolution, which, in turn, may depend upon crystal size and crystalline form.

Alternatively, delayed absorption of a parenterally administered GNE-encoding sequence may be accomplished by dissolving or suspending the composition in an oil vehicle. Injectable depot forms may be prepared by forming microencapsule or microencapsulation matrices of the expression vector in a biodegradable polymer such as polylactide-polyglycolide. Depending upon the ratio of the expression vector material to polymer and the nature of the particular polymer employed, the rate of the expression vector release can be controlled. Examples of other biodegradable polymers include poly (orthoesters) and poly(anhydrides). As described above, depot injectable formulations may also be prepared by entrapping the expression vector in liposomes (or even microemulsions) that are compatible with the target body tissues, such as muscular tissue.

In addition to methods for modulating the production of sialic acid in a system, the present invention further encompasses methods for expressing the GNE enzyme in a system. According to such embodiments, the system (e.g., the muscle cells of a human patient) may comprise an expression vector encoding GNE with a variation (e.g., GNE-R263Q). In other words, the present invention includes providing, for example, a cell or muscular tissue that harbors a mutated GNE-encoding sequence. The GNE encoding sequence may be delivered to such a system using, for example, the expression vector described herein, via parenteral injection.

According to additional related embodiments of the present invention, methods for treating, preventing, and/or ameliorating the effects of disease are provided. Such methods generally comprise providing a patient with a therapeutically effective amount of a GNE-encoding polynucleotide or effective amount of GNE protein (or polypeptide) enzyme. In certain embodiments, the GNE polynucleotide or protein molecule may, preferably, be delivered to a patient in connection with a nanoparticle and a carrier as that of lipoplex, glycoplex, liposomal, glycosomal, or other nanoparticle(s) and Formulated with carriers or Advance such as Plasma-Lyte®, to formulate a composition for parenteral routes of administration. In a non-obvious but useful embodiment, the drug vector nanoparticles, at the pH of the composition, comprises a net negative Zeta potential.

In one aspect of the invention, a pharmacologic product or composition comprising at least a polynucleotide (DNA) molecule or at least a polypeptide molecule encoding a UDP-GlcNAc 2-Epimerase/ManNAc Kinase enzyme (GNE), or a therapeutically active protein fragment thereof, in which the molecules comprise a sequence having at least one mutation or variation within the allosteric domain of GNE is provided. In another aspect of the invention, a DNA molecule encoding a UDP-GlcNAc 2-Epimerase/ManNAc Kinase enzyme (GNE) or a biologically active fragment thereof, in which the molecule comprises a sequence having at least one mutation or variation within the allosteric domain of GNE is provided.

In one aspect of the invention, the use of a polynucleotide molecule having the sequence described herein (for example SEQ ID NO: 1 or 2) or encoding an amino acid sequence described herein (for example any one or more of SEQ ID NO: 3-17), for the manufacture of a medicament for the treatment of a disease condition that benefits from increased sialic acid production is provided.

The phrase "therapeutically active fragment" or "biologically active fragment" refers to a protein or DNA fragment that maintains a level of activity within a biological system or cell in a way that leads to improved or increased sialic content and/or leads to improvement of disease condition irrespective of detectable improvement is sialic production or content. The phrase "therapeutically effective amount" refers to a sufficient amount of the polynucleotide or polypeptide (disclosed by the present invention) to express or provide sufficient levels of GNE enzyme, at a reasonable benefit-to-risk ratio, to increase sialic acid production in the targeted cells and/or to otherwise treat, prevent, and/or ameliorate the effects of disease in a patient. It will be understood, however, that the total daily usage of therapeutic and related compositions of the present invention will be decided by the attending physician, within the scope of sound medical judgment.

One of the advantages of the methods described herein is that, because the polynucleotides are administered to the affected limb directly, as opposed to a systemic administration, the therapeutically effective amount that is administered is less than that in the methods described previously. Therefore, the present methods reduce or eliminate many of the side effects that are associated with the methods described previously.

The specific therapeutically effective dose level for any particular patient may depend upon a variety of factors, including the severity of a patient's disorder; the activity of the specific GNE-encoding sequence employed; the delivery vehicle employed; the age, body weight, general health, gender and diet of the patient; the time of administration, route of administration, and rate of excretion of the specific polynucleotide or polypeptide employed; the duration of the treatment; drugs used in combination or contemporaneously with the specific GNE-encoding sequence employed; and like factors well-known in the medical arts.

Upon improvement of a patient's condition, a maintenance dose of a GNE-encoding product may be administered, if necessary. Subsequently, the dosage or frequency of administration, or both, may be reduced, as a function of the symptoms, to a level at which the improved condition is retained when the symptoms have been alleviated to the desired level.

According to yet further embodiments of the invention, novel compositions are provided for expressing GNE in a system. The compositions preferably comprise a GNE-encoding nucleic acid sequence. As described herein, the GNE-encoding nucleic acid sequence may comprise various transcriptional control elements, such as a promoter, termination sequence, and others. A non-limiting example of a composition encompassed by the present invention includes the expression vectors described herein (FIGS. 1 and 2). so as described relative to other embodiments of the present invention, the GNE-encoding nucleic acid sequence may be disposed within or connected to an appropriate vehicle for delivery to a system, such as a liposome or lipid nanoparticle. Still further, according to such embodiments, the delivery vehicle may, optionally, be decorated with agents that are capable of recognizing and binding to target cells or tissues, such as muscle cells or muscle tissues.

EXAMPLES

Example 1—Expression of Exogenous GNE in CHO-Lec3 Cells

In the following example, several GNE expression vectors from human cDNA were created. Three different GNE forms, wild type, M712T, and R266Q, were robustly expressed in GNE deficient cells (Lec3 cells). All enzymes demonstrated similar protein expression levels, albeit distinct enzymatic activities. As the following will show, the transfected GNE expressing cell lines produced significantly more sialic acid than untransfected cells. In another embodiment of the invention, an expression vector comprising a GNE sequence with a disease causing mutation (e.g. p.M712T or p.M743T) will likely provide adequate efficacy and safety, and reasonable risk-to-benefit, to be used for production of sialic acid or for treating a disease condition.
Methodology
First Procedure:

GNE Cloning. Parental vectors containing the GNE cDNA were provided by Daniel Darvish (HIBM Research Group, Encino, CA) and included GNE clones of wild type, p.M712T mutant, and p.R266Q (R266Q mutant). The destination expression vectors disclosed herein were used. The subcloning vector, pDrive (Qiagen, Valencia, CA)1 was used to shuttle the GNE clones from the parent vector to the destination vector.

GNE cDNA inserts (wildtype and M712T) were produced by reverse transcription of RNA isolated from patient whole blood. The R266Q isoform was produced using standard mutagenesis PCR techniques using specifically designed primers. cDNA was then amplified using specifically designed primers bearing the needed enzyme recognition sites at 5' tails, and subsequently subcloned into the expression vectors by T4 ligation (Invitrogen). Competent *E. coli* cells (Invitrogen) were then transformed with the expression vector.

Positive GNE clones (expression vectors bearing the GNE clone insert) were grown overnight in *E. Coli* host bacteria at 37° C. in 6% sucrose selection media containing 2 g tryptone (or soy peptone free of animal products), 1 g yeast extract, QS to 176 mL with H2O, and 60 mL of 50% sucrose (filter-sterilized with a 0.2 micron). Qiagen (Valencia, CA) HiSpeed Plasmid Maxi kit was used according to the manufacturer protocols. Alternatively, SOC medium can be used according to the manufacturer protocols.

Cell Culture: GNE-deficient CHO-Lec3 cells were grown at 37° C. in 5% CO2 in -MEM media supplemented with 4 mM L-glutamine and 10% heat inactivated, Fetal Bovine Serum. Cells for transient transfections were plated at 1×106 cells per well in 6-well plates and grown overnight. Lec3 cells were weaned to reduced serum conditions by reducing the FBS by 2.5% per passage.

Transient Transfections: Lec3 cells were transfected for 6 hours with DNA:lipid complex per well in OptiMEM (Invitrogen, Carlsbad CA), then the media was changed to normal -MEM growth media and the cells were cultured overnight. DNA:lipid complexes were formed by mixing 4 μg DNA+ 10 μl Lipofectamine 2000 (Invitrogen) according to the manufacturer's protocol. Twenty-four hours post-transfection, cells were harvested by trypsin digest and washed once with PBS before subsequent western blot or enzyme/sugar assays.

Sialic Acid Quantitation: Approximately 4×106 cells were used for the quantification of membrane-bound sialic acid by the thiobarbituric acid method. Cells were resuspended in water and lysed by passage through a 25 gauge needle 20 times and centrifuged. The supernatant was used for Bradford protein estimation and the remaining pellet was resuspended in 100 μl 2M acetic acid and incubated for 1 hour at 800 C to release glycoconjugate-bound sialic acids. 137 μl of periodic acid solution (2.5 mg/ml in 57 mM H2SO4) were added and incubated for 15 minutes at 37° C. Next, 50 μl of sodium arsenite solution (25 mg/ml in 0.5 M HCI) were added and the tubes were shaken vigorously to ensure complete elimination of the yellow-brown color. Following this step, 100 μl of 2-thiobarbituric acid solution (71 mg/ml adjusted to pH 9.0 with NaOH) were added and the samples were heated to 100° C. for 7.5 minutes. The solution was extracted with 1 ml of butanol/5% 12M HCI and the phases were separated by centrifugation. The absorbance of the organic phase was measured at 549 nm. The amount of sialic acid was measured as nmol sialic acid/mg of protein.

Second Procedure:

The following procedure is an alternative procedure to the one described above.

Cell culturing and biological assay testing: Lec3 CHO cells were initially grown in -MEM media containing 10% fetal bovine serum (FBS) (Invitrogen), received subsequent passages of -MEM FBS medium by 2.5% decrements until 0% FBS, and trypsinized prior to transfection. Four sets of transfections were prepared in triplicate using 2.0×106 CHO cells, 2.5 mL of Freestyle Media (Invitrogen), 500 μl of Opti-MEM (Invitrogen), 10 μl of Lipofectamine (Invitrogen) and 4 μg of DNA (except for the no vector set) and incubated at 37° C. in 5% CO2. Sets prepared included expression vectors with GNE-wild-type, GNE-M712T, GNE-R266Q, empty vector, and no vector media. Cells were collected 48 hours post-transfection, washed with PBS, and resuspended in lysis buffer. Sialic acid content was detected using a modified version of the Leonard Warren method (Warren 1959) and measured with NanoDrop-1000 Spectrophotometer (Thermo Fisher Scientific) at 549 nm using the UBV-Vis module. A standard curve was created with known sialic acid concentrations and denoted a clear linear association between absorbance and sialic acid concentration.

GNE clones: The GNE cDNA clones that were tested included a human wild type cDNA and two human mutant cDNAs. The mutants included the M712T GNE deficient clone and the R266Q sialuria clone. Sialuria is a human disease caused by point mutations in the CMP-sialic acid binding site of GNE, leading to a loss of feedback inhibition and mass production of sialic acids. GNE cDNAs were subcloned from their original vectors to the expression vector by restriction digest cloning. Clones were screened by directional restriction enzyme digest to confirm the GNE insert was in the correct orientation. Positive clones were sequenced in both orientations to confirm that no mutations occurred during the cloning process. The resulting chromatograms were compared against the GNE sequence from GenBank (accession #NM_005467) and the wild type did not exhibit any mutations, while the M712T and R266Q clones contained only the expected point mutations. Positive GNE clones were scaled using a maxi prep plasmid purification procedure and sequenced again to confirm that no mutations occurred. These DNA stocks were used for all subsequent experiments.

GNE mRNA quantitation: cells were grown in 10% serum and transiently transfected for 24 hours to quantitate the amount of recombinant GNE RNA that was expressed. Total RNA was extracted and RT-qPCR was performed to amplify a fragment from the exogenous GNE transcript. Serial dilutions were used to determine that the concentration of GNE expressed in transfected Lec3 cells was equal to 4.1 pg/μl. The dynamic range of the qPCR was from 5 ng-5 fg and there was no GNE mRNA product detected in control (untransfected) CHO-Lec3 cells (the cT value for untransfected cells was greater than 42 cycles, which is less than 5 fg). Therefore, recombinant GNE mRNA expression was detected in transfected Lec3 cells, while untransfected cells had undetectable amounts of GNE mRNA.

Sialic acid assays: Transfected Lec3 cells also were tested for cell surface sialic acid expression. All Lec3 samples had approximately 6.0 nmol/mg membrane bound sialic acid, with the exception of Lec3 cells transfected with the R266Q GNE which had a 1.5-3.0 fold higher amount. The R266Q GNE lacks the feedback inhibition of GNE and is known to cause an overproduction of intracellular sialic acids. No significant differences between wild type (wt) and M712T GNE were observed.

Comparison of GNE vectors: Transfection studies comparing sialic acid production of both vectors correlated well with each other. Significantly higher production of sialic acid was noted with smaller vector. The smallest vectors described in the present invention showed significantly higher sialic production than any prior vectors we developed or tested.

Preliminary high dose plasmid toxicity: We conducted a pre-GLP toxicology study of 14 day duration on 12 mice (strain B6; FBV mixed inbred, 6 male and 6 female of age 4-10 months). Male and female mice were divided equally and randomly into experiment and control groups. The maximum feasible dose (MFD) in a mouse model was 600 μg per injection. Limitation was based on solubility of plasmid (6 ηg/μl) and total volume per injection (100 μL). Considering mouse weight of 30 g and human weight of 70 kg, the human equivalent dose (HED) for mouse dose of 600 m is 113.82 mg.

TABLE 1

|  | Frequency of infusion | Mice | Weight (g) Day 1 | Toxicity 24 h | Toxicity 48 hr | Toxicity Day 7 | Weight Day 7 | Toxicity Day 14 | Weight Day 14 | Total Plasmid Dose |
|---|---|---|---|---|---|---|---|---|---|---|
| Control Group (100 normal saline) | Every day | 1M | 29.54 | None | None | None | 28.8 | None | 28.96 | 0 |
|  |  | 1F | 29.99 | None | None | None | 26.6 | None | 26.74 | 0 |
|  | Every other day | 1M | 32.69 | None | None | None | 32.9 | None | 31.95 | 0 |
|  |  | 1F | 21.88 | None | None | None | 20.6 | None | 20.23 | 0 |
|  | Once per week (day 1 and 7) | 1M | 27.76 | None | None | None | 27.5 | None | 26.91 | 0 |
|  |  | 1F | 22.24 | None | None | None | 22.5 | None | 23.55 | 0 |
| Experiment Group (600 ug plasmid in 100 uL NS) | Every day | 1M | 27.59 | None | None | None | 26.8 | None | 27.68 | 8.4 mg |
|  |  | 1F | 27.28 | None | None | None | 24.7 | None | 21.78 | 8.4 mg |
|  | Every other day | 1M | 31.54 | None | None | None | 29.6 | None | 29.39 | 4.2 mg |
|  |  | 1F | 23.35 | None | None | None | 21.9 | None | 23.71 | 4.2 mg |
|  | Once per week (day 1 and 7) | 1M | 30.37 | None | None | None | 28 | None | 29.8 | 1.2 mg |
|  |  | 1F | 24.55 | None | None | None | 23 | None | 23.38 | 1.2 mg |

The experiment group received high dose GNE plasmid (0.6 mg suspended in 0.1 ml normal saline) administered via IV by tail vein, and the control group received 0.1 ml normal saline. The groups were further divided into 3 dose frequency groups of 2 mice (1 female, 1 male) each as follows: 1) Every day administration for 14 days, 2) Every other day administration, and 3) Once per week. All animals survived the experiment. No significant change were observed between the experiment and the control groups with respect to all measured parameters, which included body weights, temperature, food and water intake, CBC blood tests (performed at days 1 and 15). Following necropsy on day 15, no significant change in the gross pathology was observed between the experiment and the control groups with respect to 12 organs, including brain, lung, heart, liver, kidney, spleen, stomach, intestines, bladder, genitals, lymph nodes, and muscle.

Pre-Clinical GLP Toxicology and Biodistribution Studies

Pharmacology and Toxicology, Safety Studies in Two Animal Species: We have performed animal studies on two species following pre-IND meeting recommendations by US FDA. The studies were performed in compliance with GLP guidelines. Intravenous (2.5 mg/ml in mice) and HLV administration (0.7 mg/ml in dogs) did not produce overt toxicity or deaths, indicating that the no observable adverse effect level (NOAEL) dose is greater than double the dose proposed for use in human subjects. In the Beagle Dog study, total of 5 animal subjects were included (2 in placebo control group receiving normal saline, and 3 in drug group receiving plasmid). Each dog received HLV treatment of all four limbs at 40% limb volume of either normal saline or 0.7 mg/ml vector composition. The dogs were dosed once at the beginning of the 30 day study.

In the Mouse study, total of 96 animal subjects were included, of which 48 were studied for toxicology, and 48 for plasmid bio-distribution, as outlined in below table.

|  |  | Sacrificed Day | | |
|---|---|---|---|---|
| Mouse Groups | Number & Sex | 8 | 15 | 30 |
| 1. Placebo Treated (toxicology) | 9M + 9F | 3M + 3F | 3M + 3F | 3M + 3F |
| 2. Drug Treated (toxicology) | 15M + 15F | 5M + 5F | 5M + 5F | 5M + 5F |
| 3. Drug Treated (bio-distribution) | 15M + 15F | 5M + 5F | 5M + 5F | 5M + 5F |
| 4. Placebo Treated (bio-distribution) | 9M + 9F | 1M + 1F | 1M + 1F | 1M + 1F |

Each mouse received 500 uL BID tail-vein injection of either normal saline or 2.5 mg/ml vector drug composition. The mice were dosed on study days 0 and 7 of 30.

Pharmacology and Drug Distribution: When DNA plasmid (pDNA) vector is administered intravenously without isolating the limb with an external tourniquet, it is rapidly degraded. The liver is the primary organ responsible for the clearance of naked DNA (Feng Liu et al. 2007). Different groups worldwide have published studies of intravenous plasmid administration in rodents, which conclude that pDNA is rapidly degraded within minutes, and it does not lead to effective expression of the therapeutic gene in any tissues/organs (Feng Liu et al. 2007; Hisazumi et al. 2004; N Kobayashi et al. 2001; Du Clos et al. 1999; Yoshida et al. 1996; Gauthier, Tyler, and Mannik 1996; Kawabata, Takakura, and Hashida 1995; Emlen and Burdick 1988; Emlen and Mannik 1984, 1978).

Figure 5:
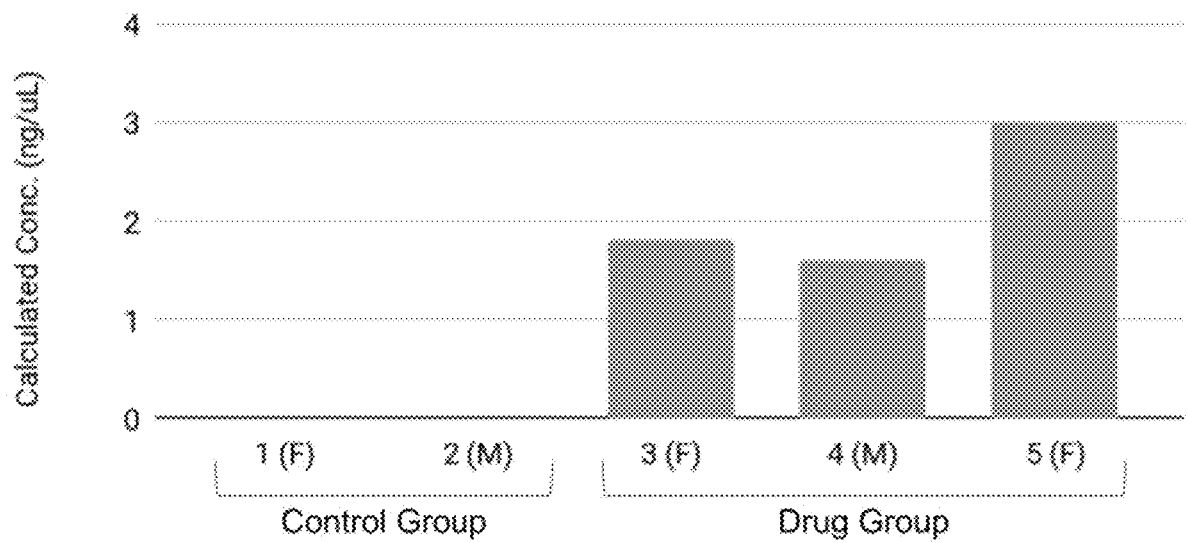
FIG. 5 shows a bar graph of drug vector by quantitative real-time PCR in the treated muscle groups of animal subjects.
Figure 6:
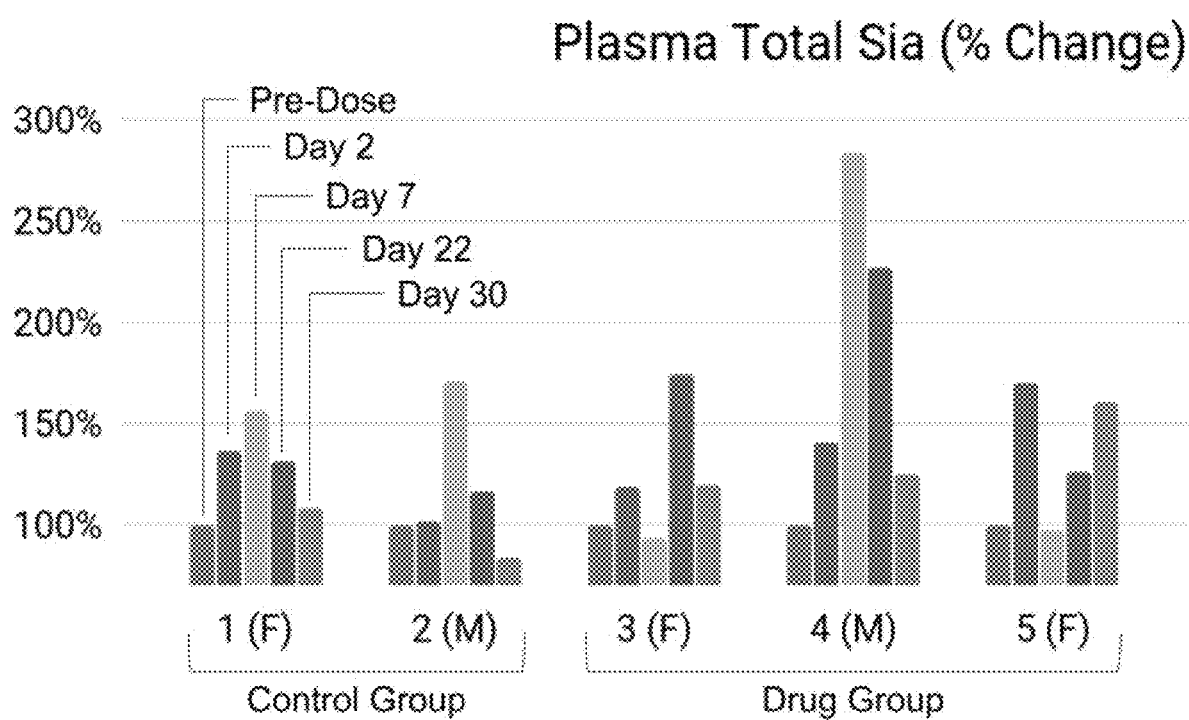
FIG. 6 shows a bar graph of relative percent change in blood plasma Sialic Acid concentration before and after treatment in animal subjects.

Beagle Dog Bio-distribution Sub-Study: The objective of this study was to assess the distribution after a single treatment to all four limbs of Beagle dogs by HLV delivery method. The drug vector active moiety distribution to selected tissues was confirmed following necropsy. The transcription of the test article (drug vector) was tested by Reverse-Transcriptase Quantitative PCR with real-time detection of human GNE (h-GNE) mRNA in five tissues of each subject (treated quadriceps skeletal muscle, untreated paraspinal skeletal muscle, liver, lung, and kidney). The transcript (mRNA of GNE) was shown to be positive in the treated limb skeletal muscles in all (3/3) of the animals in drug treated group, and negative in both (0/2) of animals in placebo control group (FIG. 5). In the bio-distribution sub-study we discovered that blood plasma sialic acid changed significantly from baseline (FIG. 6). Non-treated skeletal muscle (paraspinal) was negative in all (5/5) animals. Within the drug treated group, the lung was positive in 2/3, liver in 2/3, and both lung and liver in 1/3 of the animals (FIG. 7). Blood plasma Sialic content was measured at 2 days post-treatment, and showed a sustained treatment-related increase in all Group 2 animals. Additional testing of the plasma sialic acid at pre-dose and 30 day time points confirmed this finding, and showed a statistically significant increase at 30 days compared to control animals (p=0.092).

Mouse Plasmid Bio-distribution Sub-Study: The objective of this study was to assess the biodistribution and toxicity of the test article (drug vector) at or near maximum feasible dose (MFD) administered intravenously in male and female mice. The test article concentration (2.5 mg/ml) was injected at volumes of 0.5 ml every 12 hours (BID) by tail vein on day 0 and day 7 of the study. On Days 8, 15, and 30, the animals were euthanized and tissues procured. The tissues included injection sites (tail), skeletal muscle (quadriceps), gonads, brain, liver, kidneys, lungs, heart, spleen, and lymph nodes. Plasmid distributed was tested in every tissue by Real-Time Quantitative PCR using primers binding to the CMV-promoter region of the test article (drug vector). Besides tail and muscle tissue at sacrifice day 8 and tail tissue at sacrifice day 15, no other tissues were positive for the test article. Out of the mice sacrificed on day 8, one day post treatment, 9/10 tail (4 Female, 5 Male) and 6/10 skeletal muscle (3 F, 3 M) tissues were positive for test article. Out of the mice sacrificed at 15 days, 8 days after the last dose injected, 3/10 tail (2 F, 1 M) were positive for test article. The skeletal muscle tissues assayed were from the quadriceps. At 30 days, 23 days after last dose injected, the test article plasmid DNA was not detected in any of the tissues assayed. Since the tail vein was used for injection, the plasmid DNA detected at day 15 may be from extravasation of highly concentrated plasmid solution that persisted one week after injection. Since no tails were tested positive at day 30, any extravasated plasmid is likely cleared between 1-3 weeks post injection. Interestingly 6/10 mice tested positive for the vector in quadriceps at sacrifice day 8, one day post injection at day 7. Although rapid tail-vein injection of plasmid can lead to transcription in the liver (Budker et al. 2006), it remains unknown if slow tail-vein injection of very high dose plasmid, as used in this study, can lead to transcription in skeletal muscle of mice. Based on this study, high dose drug vector administered IV is cleared within days to 3 weeks post injection in mice.

Toxicology Integrated Summary: In two species GLP safety/toxicology studies, the maximum feasible dose (MFD) intravenous drug vector in mice (2.5 mg/ml by tail-vein) and high dose HLV administration of drug vector in Beagle Dogs (0.7 mg/ml, all four limbs treated at 40% of limb volume) did not produce overt toxicity or deaths. These studies suggest that the "no observed adverse effect level (NOAEL)" dose by either route would be greater than double the proposed human use dose (0.3-0.5 mg/ml, 25-34% of limb volume).

Beagle Dog GLP Toxicology Study Summary: The primary objective of this GLP study was to assess the potential toxicity of a test article (drug vector) after a single infused intravenous (HLV infusion) dose in male and female Beagle Dogs. Thus, we selected a relatively high dose of more than double the clinically relevant dose proposed for a human subject. All animal subjects survived and there was no notable toxicity attributable to the test article. Total of 5 Beagle dogs were enrolled. Two dogs (1 male, 1 female) were enrolled in placebo control group. Three dogs (2 females, and 1 male) were enrolled in drug treated group. On Day 1, all 4 limbs of each dog were treated via the infusion of normal saline (placebo control group, receiving 0.0 mg/ml of drug vector) or a test article solution (drug treated group, receiving 0.7 mg/ml drug vector) using the Hydrodynamic Limb Vein (HLV) administration route. 40% of the limb volume (0.4 ml/ml limb volume) was infused intravenously distal to tourniquet placement per the dosing procedure below.

| Tourniquet Pressure | Max Infusion Volume | Infusion Time | Tourniquet Duration | Plasmid dose |
|---|---|---|---|---|
| 475 mmHg | 40% of limb below tourniquet | <19 min | <20 min | 0.7 mg/ml |

All animals recovered after treatment and began using all four limbs normally within few hours following treatment of last limb. During the in-life period, the animals were observed daily for mortality and morbidity. Blood samples were collected once prior to dose administration (Day 0) and on Day 1 (4 hours post-dose), Day 2, Day 7, Day 14, Day 22, and Day 30 (prior to necropsy). Electrocardiograms (heart rate, and waveform intervals (RR, PR, QRS, QT and QTcV)) were performed on all animals prior to dose administration and on Day 29. At scheduled termination (Day 30), animals were euthanized and a complete necropsy with tissue collection and preservation was conducted. Following tissues were sent for analysis: injection sites, skeletal muscle treated limb and untreated area (e.g. back), gonads, brain, liver, kidneys, lungs, heart, spleen, bone-marrow, relevant to the injection (limbs) axillary lymph node and subcutaneous tissue around the injection site including muscle, and all other tissues with gross lesions. Tissues were embedded in paraffin wax, stained with hematoxylin and eosin, and examined microscopically.

Beagle Dog Toxicology Conclusion: Based on the results of the Beagle Dog study, a single infused intravenous (HLV Technique) dose at a rate of 0.1 cc/sec of the drug vector solution in all limbs of male and female Beagle Dogs at 0 mg/ml (Group 1) or 0.7 mg/ml (Group 2) was well-tolerated over the course of this study. No treatment-related anatomic pathology indications of target organ toxicity were identified at the dose and treatment parameters. Based on the results of the Beagle study, a single HLV dose administered at 40% of limb volume in all limbs of male and female Beagle Dogs (0 mg/ml in Group 1 control, or 0.7 mg/ml in Group 2) was well-tolerated over the course of this study (30 Days). No clinical and/or anatomic pathology indications of target organ toxicity were identified at this dose level (0.7 mg/ml) and infusion rate (0.1 ml/second).

Mouse GLP Toxicology Study Summary: The objective of this 30-day study was to assess the maximum feasible dose (MFD) of drug vector when administered intravenously by tail-vein two times per day on study Days 0 and 7. In mice, the MFD was limited by solubility/viscosity and total volume of injected. Each injection bolus was 0.5 ml administered by tail vein BID on days 0 and 7 of total 30 day study. Mouse groups 2 and 3 received the test article drug dose of 2.5 mg/ml, and groups 1 and 4 received only normal saline as placebo control. The injections were relatively slow at rate of 0.5 ml over 60 sec. The slow injection rate was to avoid transduction of the mouse liver, which is performed by rapid injection of higher volumes (1-2 ml) and lower concentrations (<0.5 mg/ml) over 5-10 seconds (Herrero et al. 2011; G Zhang, Budker, and Wolff 1999). During the in-life period, the animals were observed daily for mortality and morbidity. At scheduled termination dates, animals were euthanized and a detailed necropsy with blood and tissue collection and preservation was done. Clinical blood tests were performed (CBC, Liver/Kidney function tests) on each sacrifice day. As protocol specified, 10 tissues were harvested, including injection sites, gonads, brain, liver, kidneys, lung, heart, spleen, lymph nodes, and skeletal muscle. Tissues from groups 1 and 2 animals were embedded in paraffin wax, stained with hematoxylin and eosin, and examined microscopically.

Mouse Toxicology Conclusion: Based on the results of this study, the treatment was generally well-tolerated by male and female CD-1 mice. Reduced hepatocellular vacuolation was observed in both male and female mice on Day 8 necropsy and a single occurrence in a female mouse on Day 15. However, this change was not accompanied by degenerative or necrotizing hepatocellular injury and was not considered to be adverse by the Pathologist. No clinical and/or anatomic pathology indications of target organ toxicity were identified at the specified dose level and regiment.

Mouse Clinically Relevant and Maximum Feasible Dose (MFD) Calculations.

This section describes the reasons for selecting drug vector concentration of 2.5 mg/ml for the toxicology study. In a rodent model, the plasmid maximum feasible dose (MFD) is limited by the high volume and/or fluid-viscosity of the IV solution, and not by the total plasmid dose. The human-mouse dose equivalent calculations are listed in below table.

| | Human (70 kg) | Mouse (20 g) Equivalent Dose | 10x Mouse Equivalent Dose | Mouse Clinically Relevant Dose |
|---|---|---|---|---|
| Plasmid Dose (mg) | 490 | 1.69 | 16.87 | 1.25 |
| Max. Volume Infused (ml) | 1600 | 0.5 | 2.8* | 0.5 |
| Plasmid Concentration (mg/ml) | 0.3 | 3.37* | 6* | 2.5 |
| Infusion Duration (min) | 10 | 1 | 1 | 1 |
| Total Blood Volume (ml) | 5000 | 1 | 1 | 1 |
| Infusion: Blood Volume Ratio | 1:3 | 1:2 | 2.8:1* | 1:2 |

*Asterisk indicates limiting parameters. Mouse equivalent doses are 12.3 fold higher than human dose based on body surface area (BSA).

In HLV delivery to limb muscle, optimal dose range is 75-400 ug/g muscle (Christine Ilse Wooddell et al. 2011). Rats injected at high dose of 540 ug/g muscle (2.5 mg/ml) showed reduced vector expression and "appear to have caused some muscle damage" (Christine Ilse Wooddell et al. 2011). Similarly in mice, the expression of plasmid was noticeably lower at doses greater than 1,000 ug/g muscle (Christine Ilse Wooddell et al. 2011). A human of 70 kg has lower extremity lean muscle mass of 7-10 kg (Fuller, Laskey, and Elia 1992; Kaysen et al. 2005). The high dose of 540 ug/g muscle roughly translates to 2.35 mg/ml when 40% of limb volume is 2,300 ml. The suggested minimum dose of 75 ug/g muscle mass translates to 0.3 mg/ml plasmid concentration in same human. Based on this information, the clinically relevant dose range would be at pDNA concentrations of 0.3-2.3 mg/ml. Thus, in mice we elected to test the highest clinically relevant dose plasmid/saline concentration of 2.5 mg/ml.

Mouse Volume Guidelines: This section describes the reasons for selecting the maximum IV bolus volume of 500 uL for the toxicology study. This dose is also likely to be the MFD due to viscosity of the final solution and the total volume that can be safely injected in a mouse model. For acute intravenous injection in mouse, volume is recommended to be at maximum 200 uL (Wolfensohn and Lloyd 2003).

| Mouse Volume Guideline | ml |
|---|---|
| Max. Acute IV injection | 0.2 |
| Total Blood Volume | 1.0-2.4 |
| Safe Bleeding Volume | 0.1-0.2 |
| Total Bleed-out Volume | 0.6-1.4 |

Volumes as high as 2.5 ml have been injected rapidly (7-10 seconds) to achieve hydrodynamic liver transfection (G Zhang, Budker, and Wolff 1999; F Liu, Song, and Liu 1999). The use of normal saline instead of Ringer's solution resulted in 40% mouse mortality (G Zhang, Budker, and Wolff 1999). Infusion >1 ml is considered to be extreme because it can exceeds total blood volume and cardiac output, leading to transient right sided congestive heart failure (G Zhang, Budker, and Wolff 1999), and liver toxicity (8.2% of hepatocytes of half the mice were necrotic). Such effect is desired when drastic swelling of the liver is needed for liver transfection (Naoki Kobayashi, Nishikawa, and Takakura 2005). Thus, for clinically relevant highest dose and MFD plasmid/saline infusion, we selected the bolus volume of 500 uL in mice.

Drug Vector Manufacturing and In-Vitro Bioactivity

Manufacturing Specifications: H002 vectors are manufactured in accordance with Good Manufacturing Practice (GMP) for clinical studies. H002 is produced using a process involving scale up and purification suitable for clinical use, manufactured with the final specifications described herein.

| | DNA Purity (A260/280) | Supercoiled (ccc) | Bacterial DNA | Endotoxin (EU/mg) |
|---|---|---|---|---|
| Specifications | 1.7-2.0 | >90% | <1.3% | <0.5 |

To achieve endotoxin administration of less than 5 EU/kg/hr in a living biological organism, the final composition endotoxin levels are below 0.5 EU/mg. Residual bacterial host genomic DNA is less than 1.3% by quantitative PCR because higher levels has been suspected to cause occult necrosis when administered by HLV route of administration (Wooddell et. al. 2012).

In-Vitro Bioactivity: GNE is the rate limiting enzyme of Sialic Acid (Sia) biosynthesis. This enzyme is expressed by all mammals (including humans), in several isoforms comprising 612-753 amino acids. GNE has three functional domains: (1) Epimerase domain (2) Kinase domain, and (3) Allosteric negative feedback (inhibitory) domain. The bioactivity of GNE was verified using a cell line deficient in GNE activity, and has been shown to increase cellular sialic acid production (Jay et al. 2008). The bioactivity of H002 vectors have been determined by transfection of mammalian cells unable to produce sialic acid caused by lack of endogenous Gne activity (Jay et al. 2008). The plasmids demonstrated robust sialic production in GNE-deficient cells cultivated in 2.5% fetal bovine serum (FBS) (Jay et al. 2008). These results have been subsequently repeated using optimized culture environment suited for the assay, including weaning of cells from sialic containing FBS medium.

Stability, Storage, and Shelf Life of the Pharmaceutical Composition: H002 vectors remains stable for over 13 months when stored at −80 C, and up to 4 months when stored at 4 C, which is similar to pDNA vectors (Walther et al. 2003). The supercoiled or covalently closed circular (ccc) form of pDNA breaks down to the open circular (oc) form after 4 months when stored at 4 C. Specific stability study for H002 vectors is comparable to other pDNA of similar size and concentration. Sufficient quantity of H002 vectors can be manufactured on a per patient basis, and used within 1-3 months of manufacturing production. The H002 vectors may be stored at −80 C temperature and thawed at room temperature before use in a human or animal subject.

AAV Vectors

In other embodiments of the invention, the drug vector is an Adeno-Associated Virus (AAV), or more specifically a recombinant AAV (rAAV, herein AAV is used to imply either AAV or rAAV) with specific features needed for effective transduction of tissues and organs requiring increased sialic or GNE activity, such as skeletal muscle that has a reduced amount of cell surface sialic acid content. Most AAV vectors require the presence of adequate amount of sialic acid for effective cellular transduction.

Specific AAV serotypes which require galactose in instead of sialic (Bell et. al. 2012), and hybrid or chimeric glycan-binding AAV vectors (Shen et. al. 2013-2014), which are able to enter a cell and transfect without the need for cell surface sialic acid are likely to be critical for the development of effective gene therapy or enzyme replacement therapy for diseases such as GNE myopathy. Sialic acid is the most common terminal sugar on glycans which make up the glycocalyx. This terminal sialic acid often covers galactose, and in disease conditions lacking adequate amount of sialic, the galactose is exposed instead of sialic.

In an AAV capsid, the amino acids that would be critical and make up the galactose binding site include Asp-271, Asn-272, Tyr-446, Asn-470, (optionally Ala-472, Val-4730 and Trp-503. These are the amino acid requirements for AAV capsid to enable binding to galactose instead of sialic. These amino acids at the specific positions are required for enabling galactose binding that form a molecular pocket at the base of the protrusions around the icosahedral 3-fold axes of symmetry (Bell et. al. 2012, Shen et. al. 2013-2014). Because AAV9 has this molecular pocket comprising the required amino acid residues, the enzymatic removal of terminal sialic from cell surface glycan increases AAV9 transduction regardless of cell type, and resialylation of galactosylated glycans on the sialic acid-deficient cells partially blocked AAV transduction (Shen et. al. 2011).

To effectively treat GNE myopathy, or other diseases of low sialic cell surface content, similar molecular pocket as found on AAV9 is needed, thus forming a pocket at the base of the protrusions around the icosahedral 3-fold axes of symmetry, comprising analogous amino acid residues at positions in relation to each other in a sequence "Asp-Asn-(173*Xaa, meaning 173 of any amino acid)-Tyr-(23*Xaa)-Asn-Xaa (optionally Ala-Val)-(29*Xaa)-Trp". These amino acid sequences are described by SEQ ID NO: 18 and SEQ ID NO: 19. Our preliminary research data shows AAV vector comprising the foregoing amino acid sequence and at least one expression vector disclosed by FIGS. 1 and 2 and SEQ ID NO: 1 and SEQ ID NO: 2 (referred to as AAV-H002 vectors), provides higher transfection rate and higher sialic production in a hypo-sialylated or under-sialylated mammalian cell. Based on preliminary research data, the hypo-sialylated mammalian cells show lower transfection rates and lower sialic production when transfected by other AAV vectors (lacking foregoing amino acid sequence) then when transfected by AAV-H002 vector. In one embodiment of the invention, the AAV-H002 vectors would be effective in treating GNE myopathy and other diseases that are in need of, or can benefit from, increased sialic biosynthesis. In other embodiments of the invention, a pharmacologic composition that uses AAV-H002 in manufacturing, or comprising AAV-H002 vector in final product formulation, is expected to show a favorable or reasonable risk-benefit portfolio, or show a wide therapeutic window. Unlike GNE-Lipoplex (Phadke et. al. 2009, Nemunaitis et. al. 2011), which shows dose-limiting toxicity at doses of 8.0-20.0 mg per injection, the stated embodiments of a pharmacologic composition, that uses or comprises AAV-H002, would not show clinically relevant dose-limiting toxicity. In one aspect of the invention, even at high doses such as maximum feasible dose (MFD) or maximum tolerated dose (MTD), the stated pharmacologic composition is expected to show favorable or reasonable risk-benefit portfolio. In another aspect of the invention, a pharmacologic composition that uses AAV-H002 in manufacturing, or comprising AAV-H002 vector in final product formulation, causes higher transduction and sialic production within a living organism than any other composition known to date.

In other embodiments, AAV12 can be used having a yet unknown but different mechanism for sialic-independent or HSPG-independent mechanism, but similar to AAV2, cell entry of AAV12 is likely mediated by receptor-mediated endocytosis, and release from the endosomes requires endosomal acidification (Schmidt et. al. 2008). In one embodiment of the invention, AAV12 comprises at least one GNE expression vector (FIGS. 1 and 2) disclosed herein. Such AAV12 vector comprising the GNE expression vector (referred to as AAV12-H002 vectors) would be able to transfect hypo-sialylated cells. In other embodiments of the invention, the AAV12-H002 vectors would be effective in treating GNE myopathy and other diseases that are in need of, or can benefit from, increased sialic biosynthesis. In another embodiment of the invention, a pharmacologic composition that uses AAV12-H002 in manufacturing, or comprising AAV12-H002 vector in final product formulation, is expected to show a favorable or reasonable risk-benefit portfolio. In one aspect of the invention, even at high doses such as maximum feasible dose (MFD) or maximum tolerated dose (MTD), a pharmacologic composition using or comprising AAV12-H002 is expected to show favorable or reasonable risk-benefit portfolio. In another aspect of the invention, a pharmacologic composition that uses AAV12-H002 in manufacturing, or comprising AAV12-H002 vector in final product formulation, causes higher therapeutic gene transduction, and higher sialic production, within a living organism than other compositions that use or comprise another AAV vector that is sialic-dependent for cell entry.

An additional and important clinical advantage for using ROA Hydrodynamic Infusion to deliver AAV is reduced immune toxicity and long term expression of the therapeutic transgene. Using the AAV vector, HLV-like delivery termed Regional Intravenous (RI) has shown to have significant advantages compared to IM delivery (Toromanoff et al. 2008), and leads to reduced chance of immune-toxicity in non-human primates. IM route of administration of AAV vectors are consistently associated with immunotoxicity and the destruction of the genetically modified myofibers, whereas HLV-like delivery, as described ROA Hydrodynamic Infusion herein, allows for stable expression of the transgene using an AAV vector (Toromanoff et al. 2010). In other aspects of the invention, the Hydrodynamic Infusion ROA of a pharmaceutical composition described above (using AAV-H002 or AAV12-H002 in manufacturing, or comprising AAV-H002 or AAV12-H002), reduces chance of deleterious or undesired host immune response, such as immune toxicity or limiting the effectiveness of treatment. In other embodiments of the invention, the clinical use of ROA Hydrodynamic Infusion will allow for more effective inducement of host immune tolerance, thereby enabling re-dosing a subject who has been previously exposed to AAV-H002 or AAV12-H002. In one aspect of the invention, re-dosing of same subject leads to additive sequential increase in the expression of therapeutic GNE enzyme (i.e. each dose increases the therapeutic effect instead of becoming ineffective or causing adverse effect due to an undesired host immune response).

Below table described the receptor binding sites identified for various AAV capsid serotypes (Srivastava 2016, Santiago-Ortiz et. al. 2015, Naso et. al. 2017, Mietzsch et. al. 2014, Bell et. al. 2012, Vandenberghe et. al. 2009, Quinn et. al. 2011, and Schmidt et. al. 2008).

| Capsid Serotype | Receptor binding site | Example target tissue(s) |
| --- | --- | --- |
| AAV1 | Sialic, N-linked sialic | Muscle, liver, joint, heart |
| AAV2 | HSPG, αVβ5 integrin, FGFR1, laminin receptor (LamR) | Lung, muscle, CNS, liver, joint, eye |
| AAV2.5 | Heparan Sulfate Proteoglycan (HSPG) | Muscle |
| AAV3 | HSPG, LamR | |
| AAV4 | Sialic, O-linked sialic | Eye, CNS |
| AAV5 | Sialic, N-linked sialic, platelet-derived growth factor receptor (PDGFR) | Eye, CNS, lung, liver |
| AAV6 | Sialic, N-linked sialic, epidermal growth factor receptor (EGFR) | Muscle, heart, liver, lung |
| AAV7 | Unidentified glycan | Muscle, liver |
| AAV8 | LamR | Muscle, liver, eye |
| AAV9 | Galactose, LamR | Liver, lung, heart, muscle |
| AAVrh.10 | Unidentified glycan | Lung, CNS |
| AAV12 | Endosomal acidification, independent of Sialic or HSPG | Nasal epithelia, muscle, salivary gland |
| AAV13 | HSPG, Acetylated, 2/6-O-sulfated heparin | |

SUMMARY STATEMENT

The present invention described herein, discloses, teaches, and enables the development and manufacturing of a pharmaceutical composition with a high likelihood for clinical efficacy, acceptable safety, while allowing for repeat administration in the same subject to achieve higher expression levels in target tissue or organ by the described ROA Hydrodynamic Infusion. In the present invention, we have disclosed critical features and elements of the drug vector, in addition to disclosing, teaching, and enabling specific modifications of the ROA Hydrodynamic Infusion, to make possible the development of an effective and safe pharmacologic product or composition.

Throughout the description and specification of the invention herein, unless clearly stated otherwise, words such as nucleic acid or amino acid "sequence" in the context of a composition or product or construct, will be understood to imply that the composition, product, or construct comprises a polynucleotide or polypeptide molecule having such sequence. Unless clearly stated otherwise, the words pharmacologic or pharmaceutical composition or product, medicament, drug, therapeutic composition or product, and similar words are used interchangeably to refer to a composition (such as a gene therapy vector or an enzyme replacement therapy) for administration to a human or animal subject in a healthcare facility such as clinic or hospital.

Throughout the description and specification of the invention herein, unless clearly stated otherwise, words such as "comprise" or "include" or variations such as "comprises" or "comprising" or "includes" or "including", will be understood to imply the inclusion of the stated features or integers, but not the exclusion of any other feature or integer or group of features or integers.

Although illustrative embodiments of the present invention have been described herein, the invention is not limited to those described, and that various other changes or modifications may be made by one skilled in the art without departing from the scope or spirit of the invention. The invention has been described in some detail by way of illustration and example for purposes of clarity of understanding, thus teaching those skilled in the art that other changes or modification that is not specifically stated herein can be made. Therefore, the description and examples should not be construed as limiting the scope of the invention.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

SEQUENCE LISTING

```
<160> NUMBER OF SEQ ID NOS: 19

<210> SEQ ID NO 1
<211> LENGTH: 3838
<212> TYPE: DNA
<213> ORGANISM: Homo sapiens
<220> FEATURE:
<221> NAME/KEY: misc_feature
<222> LOCATION: (2301)..(2303)
<223> OTHER INFORMATION: n is a, c, g, or t
<220> FEATURE:
<221> NAME/KEY: misc_feature
<222> LOCATION: (2310)..(2312)
<223> OTHER INFORMATION: n is a, c, g, or t

<400> SEQUENCE: 1
ccgcctaatg agcgggcttt tttttggctt gttgtccaca accgttaaac cttaaaagct      60
ttaaaagcct tatatattct ttttttcett ataaaactta aaaccttaga ggctatttaa     120
gttgctgatt tatattaatt ttattgttca aacatgagag cttagtacgt gaaacatgag     180
agcttagtac gttagccatg agagcttagt acgttagcca tgagggttta gttcgttaaa     240
catgagagct tagtacgtta aacatgagag cttagtacgt actatcaaca ggttgaactg     300
ctgatccacg ttgtggtaga attggtaaag agagtcgtgt aaaatatcga gttcgcacat     360
cttgttgtct gattattgat ttttggcgaa accatttgat catatgacaa gatgtgtatc     420
taccttaact taatgatttt gataaaaatc attaggtacc ccggctctag ttattaatag     480
taatcaatta cggggtcatt agttcatagc ccatatatgg agttccgcgt tacataactt     540
acggtaaatg gcccgcctgg ctgaccgccc aacgacccc gcccattgac gtcaataatg     600
acgtatgttc ccatagtaac gccaataggg actttccatt gacgtcaatg ggtggagtat     660
ttacggtaaa ctgcccactt ggcagtacat caagtgtatc atatgccaag tacgccccct     720
attgacgtca atgacggtaa atggcccgcc tggcattatg cccagtacat gaccttatgg     780
gactttccta cttggcagta catctacgta ttagtcatcg ctattaccat ggtgatgcgg     840
ttttggcagt acatcaatgg gcgtggatag cggtttgact cacggggatt tccaagtctc     900 cacccccattg acgtcaatgg gagtttgttt tggcaccaaa atcaacggga ctttccaaaa     960
tgtcgtaaca actccgcccc attgacgcaa atgggcggta ggcgtgtacg gtgggaggtc    1020
tatataagca gagctcgttt agtgaaccgt cagatcgcct ggagacgcca tccacgctgt    1080
tttgacctcc atagaagaca ccgggaccga tccagcctcc gcggctcgca tctctccttc    1140
acgcgcccgc cgccctacct gaggccgcca tccacgccgg ttgagtcgcg ttctgccgcc    1200
tcccgcctgt ggtgcctcct gaactgcgtc cgccgtctag gtaagtttaa agctcaggtc    1260
gagaccgggc ctttgtccgg cgctcccttg gagcctacct agactcagcc ggctctccac    1320
gctttgcctg accctgcttg ctcaactcta gttctctcgt taacttaatg agacagatag    1380
aaactggtct tgtagaaaca gagtagtcgc ctgcttttct gccaggtgct gacttctctc    1440
ccctgggctt ttctctttt ctcaggttga aagaagaag acgaagaaga cgaagaagac    1500
```

```
aaaccgtcgt cgacatggag aagaatggaa ataaccgaaa gctgcgggtt tgtgttgcta    1560
cttgtaaccg tgcagattat tctaaacttg ccccgatcat gtttggcatt aaaaccgaac    1620
ctgagttctt tgaacttgat gttgtggtac ttggctctca cctgatagat gactatggaa    1680
atacatatcg aatgattgaa caagatgact ttgacattaa caccaggcta cacacaattg    1740
tgaggggaga agatgaggca gccatggtgg agtcagtagg cctggcccta gtgaagctgc    1800
cagatgtcct taatcgcctg aagcctgata tcatgattgt tcatgagac aggtttgatg     1860
ccctggctct ggccacatct gctgccttga tgaacatccg aatccttcac attgaaggtg    1920
gggaagtcag tgggaccatt gatgactcta tcagacatgc cataacaaaa ctggctcatt    1980
atcatgtgtg ctgcacccgc agtgcagagc agcacctgat atccatgtgt gaggaccatg    2040
atcgcatcct tttggcaggc tgcccttcct atgacaaact tctctcagcc aagaacaaag    2100
actacatgag catcattcgc atgtggctag gtgatgatgt aaaatctaaa gattacattg    2160
ttgcactaca gcaccctgtg accactgaca ttaagcattc cataaaaatg tttgaattaa    2220
cattggatgc acttatctca tttaacaagc ggaccctagt cctgtttcca atatattgacg   2280
cagggagcaa agagatggtt nnngtgatgn nnaagaaggg cattgagcat catcccaact    2340
ttcgtgcagt taaacacgtc ccatttgacc agtttataca gttggttgcc catgctggct    2400
gtatgattgg gaacagcagc tgtggggttc gagaagttgg agcttttgga cacctgtga     2460
tcaacctggg aacacgtcag attggaagag aaacagggga gaatgttctt catgtccggg    2520
atgctgacac ccaagacaaa atattgcaag cactgcacct tcagtttggt aaacagtacc    2580
cttgttcaaa gatatatggg gatggaaatg ctgttccaag gattttgaag tttctcaaat    2640
ctatcgatct tcaagagcca ctgcaaaaga aattctgctt tcctcctgtg aaggagaata    2700
tctctcaaga tattgaccat attccttgaaa ctctaagtgc cttggccgtt gatcttggcg    2760
ggacgaacct ccgagttgca atagtcagca tgaagggtga aatagttaag aagtatactc    2820
agttcaatcc taaaacctat gaagagagga ttaattaat cctacagatg tgtgtggaag     2880
ctgcagcaga agctgtaaaa ctgaactgca gaattttggg agtaggcatt tccacaggtg    2940
gccgtgtaaa tcctcgggaa ggaattgtgc tgcattcaac caaactgatc caagagtgga    3000
actctgtgga ccttaggacc ccccttctg acactttgca tctccctgtg tgggtagaca     3060
atgatggcaa ctgtgctgcc ctggcggaaa ggaaatttgg ccaaggaaag ggactggaaa    3120
actttgttac acttatcaca ggcacaggaa tcggtggtgg aattatccat cagcatgaat    3180
tgatccacgg aagctccttc tgtgctgcag aactgggcca ccttgttgtg tctctggatg    3240
ggcctgattg ttcctgtgga agccatgggt gcattgaagc atacgcctct ggaatggcct    3300
tgcagaggga ggcaaaaaag ctccatgatg aggacctgct cttggtggaa gggatgtcag    3360
tgccaaaaga tgaggctgtg ggtgcgctcc atctcatcca agctgcgaaa cttggcaatg    3420
cgaaggccca gagcatccta agaacagctg gaacagcttt gggtcttggg gttgtgaaca    3480
tcctccatac catgaatccc tcccttgtga tcctctccgg agtcctggcc agtcactata    3540
tccacattgt caaagacgtc attcgccagc aggccttgtc ctccgtgcag gacgtggatg    3600
tggtggtttc ggatttggtt gaccccgccc tgctgggtgc tgccagcatg gttctggact    3660
acacaacacg caggatctac tagtaagatc tttttccctc tgccaaaaat tatggggaca    3720
tcatgaagcc ccttgagcat ctgacttctg gctaataaag gaaatttatt ttcattgcaa    3780
tagtgtgttg gaatttttg tgtctctcac tcggaaggac ataagggcgg ccgctagc      3838
```

<210> SEQ ID NO 2
<211> LENGTH: 4032
<212> TYPE: DNA
<213> ORGANISM: Homo sapiens
<220> FEATURE:
<221> NAME/KEY: misc_feature
<222> LOCATION: (2495)..(2497)
<223> OTHER INFORMATION: n is a, c, g, or t
<220> FEATURE:
<221> NAME/KEY: misc_feature
<222> LOCATION: (2504)..(2506)
<223> OTHER INFORMATION: n is a, c, g, or t

<400> SEQUENCE: 2

| | | | | | |
|---|---|---|---|---|---|
| ccgcctaatg | agcgggcttt | tttttggctt | gttgtccaca | accgttaaac | cttaaaagct | 60 |
| ttaaaagcct | tatatattct | ttttttttctt | ataaaactta | aaaccttaga | ggctatttaa | 120 |
| gttgctgatt | tatattaatt | ttattgttca | aacatgagag | cttagtacgt | gaaacatgag | 180 |
| agcttagtac | gttagccatg | agagcttagt | acgttagcca | tgagggttta | gttcgttaaa | 240 |
| catgagagct | tagtacgtta | aacatgagag | cttagtacgt | actatcaaca | ggttgaactg | 300 |
| ctgatccacg | ttgtggtaga | attggtaaag | agagtcgtgt | aaaatatcga | gttcgcacat | 360 |
| cttgttgtct | gattattgat | ttttggcgaa | accatttgat | catatgacaa | gatgtgtatc | 420 |
| taccttaact | taatgatttt | gataaaaatc | attaggatcc | gctctagcca | ctacgggtct | 480 |
| aggctgccca | tgtaaggagg | caaggcctgg | ggacacccga | gatgcctggt | tataattaac | 540 |
| ccagacatgt | ggctgccccc | cccccccccaa | cacctgctgc | ctgctaaaaa | taaccctgtc | 600 |
| cctggtggtc | tagccactac | gggtctaggc | tgcccatgta | aggaggcaag | gcctggggac | 660 |
| acccgagatg | cctggttata | attaacccag | acatgtggct | gcccccccccc | ccccaacacc | 720 |
| tgctgcctgc | taaaaataac | cctgtccctg | gtggtctagc | cactacgggt | ctaggctgcc | 780 |
| catgtaagga | ggcaaggcct | ggggacaccc | gagatgcctg | gttataatta | acccagacat | 840 |
| gtggctgccc | cccccccccc | aacacctgct | gcctgctaaa | aataaccctg | tccctggtgg | 900 |
| tctagaatca | aggctgtggg | ggactgaggg | caggctgtaa | caggcttggg | ggccagggct | 960 |
| tatacgtgcc | tgggactccc | aaagtattac | tgttccatgt | tcccggcgaa | gggccagctg | 1020 |
| tcccccgcca | gctagactca | gcacttagtt | taggaaccag | tgagcaagtc | agcccttggg | 1080 |
| gcagcccata | caaggccatg | gggctgggca | agctgcacgc | ctgggtccgg | ggtgggcacg | 1140 |
| gtgcccgggc | aacgagctga | aagctcatct | gctctcaggg | gccctccct | ggggacagcc | 1200 |
| cctcctggct | agtcacaccc | tgtaggctcc | tctatataac | caggggcac | aggggctgcc | 1260 |
| cccgggtcac | caccacctcc | acagcacaga | cagacactca | ggagccagcc | agccgcggct | 1320 |
| cgcatctctc | cttcacgcgc | ccgccgcct | acctgaggcc | gccatccacg | ccggttgagt | 1380 |
| cgcgttctgc | cgcctcccgc | ctgtggtgcc | tcctgaactg | cgtccgccgt | ctaggtaagt | 1440 |
| ttaaagctca | ggtcgagacc | gggcctttgt | ccggcgctcc | cttggagcct | acctagactc | 1500 |
| agccggctct | ccacgctttg | cctgaccctg | cttgctcaac | tctagttctc | tcgttaactt | 1560 |
| aatgagacag | atagaaactg | gtcttgtaga | aacagagtag | tcgcctgctt | ttctgccagg | 1620 |
| tgctgacttc | tctccctgg | gcttttttct | ttttctcagg | ttgaaaagaa | gaagacgaag | 1680 |
| aagacgaaga | agacaaaccg | tcgtcgacat | ggagaagaat | ggaaataacc | gaaagctgcg | 1740 |
| ggtttgtgtt | gctacttgta | accgtgcaga | ttattctaaa | cttgccccga | tcatgtttgg | 1800 |
| cattaaaaacc | gaacctgagt | tctttgaact | tgatgttgtg | gtacttggct | ctcacctgat | 1860 |
| agatgactat | ggaaatacat | atcgaatgat | tgaacaagat | gactttgaca | ttaacaccag | 1920 |

```
gctacacaca attgtgaggg gagaagatga ggcagccatg gtggagtcag taggcctggc    1980
cctagtgaag ctgccagatg tccttaatcg cctgaagcct gatatcatga ttgttcatgg    2040
agacaggttt gatgccctgg ctctggccac atctgctgcc ttgatgaaca tccgaatcct    2100
tcacattgaa ggtggggaag tcagtgggac cattgatgac tctatcagac atgccataac    2160
aaaactggct cattatcatg tgtgctgcac ccgcagtgca gagcagcacc tgatatccat    2220
gtgtgaggac catgatcgca tccttttggc aggctgccct tcctatgaca aacttctctc    2280
agccaagaac aaagactaca tgagcatcat tcgcatgtgg ctaggtgatg atgtaaaatc    2340
taaagattac attgttgcac tacagcaccc tgtgaccact gacattaagc attccataaa    2400
aatgtttgaa ttaacattgg atgcacttat ctcatttaac aagcggaccc tagtcctgtt    2460
tccaaatatt gacgcaggga gcaaagagat ggttnnngtg atgnnnaaga agggcattga    2520
gcatcatccc aactttcgtg cagttaaaca cgtcccattt gaccagttta tacagttggt    2580
tgcccatgct ggctgtatga ttgggaacag cagctgtggg gttcgagaag ttggagcttt    2640
tggaacacct gtgatcaacc tgggaacacg tcagattgga agagaaacag gggagaatgt    2700
tcttcatgtc cggatgctg acacccaaga caaaatattg caagcactgc accttcagtt    2760
tggtaaacag taccccttgtt caaagatata tggggatgga aatgctgttc caaggatttt    2820
gaagtttctc aaatctatcg atcttcaaga gccactgcaa aagaaattct gctttcctcc    2880
tgtgaaggag aatatctctc aagatattga ccatattctt gaaactctaa gtgccttggc    2940
cgttgatctt ggcgggacga acctccgagt tgcaatagtc agcatgaagg gtgaaatagt    3000
taagaagtat actcagttca atcctaaaac ctatgaagag aggattaatt taatcctaca    3060
gatgtgtgtg gaagctgcag cagaagctgt aaaactgaac tgcagaattt tgggagtagg    3120
catttccaca ggtggccgtg taaatcctcg ggaaggaatt gtgctgcatt caaccaaact    3180
gatccaagag tggaactctg tggaccttag dacccccctt tctgacactt tgcatctccc    3240
tgtgtgggta gacaatgatg gcaactgtgc tgccctggcg gaaaggaaat ttggccaagg    3300
aaagggactg gaaaactttg ttacacttat cacaggcaca ggaatcggtg gtggaattat    3360
ccatcagcat gaattgatcc acggaagctc cttctgtgct gcagaactgg gccaccttgt    3420
tgtgtctctg gatgggcctg attgttcctg tggaagccat gggtgcattg aagcatacgc    3480
ctctggaatg gccttgcaga gggaggcaaa aaagctccat gatgaggacc tgctcttggt    3540
ggaagggatg tcagtgccaa aagatgaggc tgtgggtgcg ctccatctca tccaagctgc    3600
gaaacttggc aatgcgaagg cccagagcat cctaagaaca gctggaacag ctttgggtct    3660
tggggttgtg aacatcctcc ataccatgaa tccctcccgt gtgatcctct ccggagtcct    3720
ggccagtcac tatatccaca ttgtcaaaga cgtcattcgc cagcaggcct tgtcctccgt    3780
gcaggacgtg gatgtggtgg tttcggattt ggttgacccc gccctgctgg gtgctgccag    3840
catggttctg gactacacaa cacgcaggat ctactagtaa gatctttttc cctctgccaa    3900
aaattatggg gacatcatga agcccctga gcatctgact tctggctaat aaaggaaatt    3960
tattttcatt gcaatagtgt gttggaattt tttgtgtctc tcactcggaa ggacataagg    4020
gcggccgcta gc                                                        4032
```

<210> SEQ ID NO 3
<211> LENGTH: 722
<212> TYPE: PRT
<213> ORGANISM: Homo sapiens
<220> FEATURE:
<221> NAME/KEY: misc_feature

```
<222> LOCATION: (263)..(263)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid

<400> SEQUENCE: 3
```

| | | | | | | | | | | | | | | |
|---|---|---|---|---|---|---|---|---|---|---|---|---|---|---|
| Met | Glu | Lys | Asn | Gly | Asn | Asn | Arg | Lys | Leu | Arg | Val | Cys | Val | Ala | Thr |
| 1 | | | | 5 | | | | | 10 | | | | | 15 |
| Cys | Asn | Arg | Ala | Asp | Tyr | Ser | Lys | Leu | Ala | Pro | Ile | Met | Phe | Gly | Ile |
| | | | 20 | | | | | 25 | | | | | 30 | | |
| Lys | Thr | Glu | Pro | Glu | Phe | Phe | Glu | Leu | Asp | Val | Val | Leu | Gly | Ser | |
| | | 35 | | | | | 40 | | | | | 45 | | | |
| His | Leu | Ile | Asp | Asp | Tyr | Gly | Asn | Thr | Tyr | Arg | Met | Ile | Glu | Gln | Asp |
| | 50 | | | | | 55 | | | | | 60 | | | | |
| Asp | Phe | Asp | Ile | Asn | Thr | Arg | Leu | His | Thr | Ile | Val | Arg | Gly | Glu | Asp |
| 65 | | | | | 70 | | | | | 75 | | | | | 80 |
| Glu | Ala | Ala | Met | Val | Glu | Ser | Val | Gly | Leu | Ala | Leu | Val | Lys | Leu | Pro |
| | | | | 85 | | | | | 90 | | | | | 95 | |
| Asp | Val | Leu | Asn | Arg | Leu | Lys | Pro | Asp | Ile | Met | Ile | Val | His | Gly | Asp |
| | | | 100 | | | | | 105 | | | | | 110 | | |
| Arg | Phe | Asp | Ala | Leu | Ala | Leu | Ala | Thr | Ser | Ala | Ala | Leu | Met | Asn | Ile |
| | | 115 | | | | | 120 | | | | | 125 | | | |
| Arg | Ile | Leu | His | Ile | Glu | Gly | Gly | Glu | Val | Ser | Gly | Thr | Ile | Asp | Asp |
| | 130 | | | | | 135 | | | | | 140 | | | | |
| Ser | Ile | Arg | His | Ala | Ile | Thr | Lys | Leu | Ala | His | Tyr | His | Val | Cys | Cys |
| 145 | | | | | 150 | | | | | 155 | | | | | 160 |
| Thr | Arg | Ser | Ala | Glu | Gln | His | Leu | Ile | Ser | Met | Cys | Glu | Asp | His | Asp |
| | | | | 165 | | | | | 170 | | | | | 175 | |
| Arg | Ile | Leu | Leu | Ala | Gly | Cys | Pro | Ser | Tyr | Asp | Lys | Leu | Leu | Ser | Ala |
| | | | 180 | | | | | 185 | | | | | 190 | | |
| Lys | Asn | Lys | Asp | Tyr | Met | Ser | Ile | Ile | Arg | Met | Trp | Leu | Gly | Asp | Asp |
| | | 195 | | | | | 200 | | | | | 205 | | | |
| Val | Lys | Ser | Lys | Asp | Tyr | Ile | Val | Ala | Leu | Gln | His | Pro | Val | Thr | Thr |
| | 210 | | | | | 215 | | | | | 220 | | | | |
| Asp | Ile | Lys | His | Ser | Ile | Lys | Met | Phe | Glu | Leu | Thr | Leu | Asp | Ala | Leu |
| 225 | | | | | 230 | | | | | 235 | | | | | 240 |
| Ile | Ser | Phe | Asn | Lys | Arg | Thr | Leu | Val | Leu | Phe | Pro | Asn | Ile | Asp | Ala |
| | | | | 245 | | | | | 250 | | | | | 255 | |
| Gly | Ser | Lys | Glu | Met | Val | Xaa | Val | Met | Xaa | Lys | Lys | Gly | Ile | Glu | His |
| | | | 260 | | | | | 265 | | | | | 270 | | |
| His | Pro | Asn | Phe | Arg | Ala | Val | Lys | His | Val | Pro | Phe | Asp | Gln | Phe | Ile |
| | | 275 | | | | | 280 | | | | | 285 | | | |
| Gln | Leu | Val | Ala | His | Ala | Gly | Cys | Met | Ile | Gly | Asn | Ser | Ser | Cys | Gly |
| | 290 | | | | | 295 | | | | | 300 | | | | |
| Val | Arg | Glu | Val | Gly | Ala | Phe | Gly | Thr | Pro | Val | Ile | Asn | Leu | Gly | Thr |
| 305 | | | | | 310 | | | | | 315 | | | | | 320 |
| Arg | Gln | Ile | Gly | Arg | Glu | Thr | Gly | Glu | Asn | Val | Leu | His | Val | Arg | Asp |
| | | | | 325 | | | | | 330 | | | | | 335 | |
| Ala | Asp | Thr | Gln | Asp | Lys | Ile | Leu | Gln | Ala | Leu | His | Leu | Gln | Phe | Gly |
| | | | 340 | | | | | 345 | | | | | 350 | | |
| Lys | Gln | Tyr | Pro | Cys | Ser | Lys | Ile | Tyr | Gly | Asp | Gly | Asn | Ala | Val | Pro |
| | | 355 | | | | | 360 | | | | | 365 | | | |
| Arg | Ile | Leu | Lys | Phe | Leu | Lys | Ser | Ile | Asp | Leu | Gln | Glu | Pro | Leu | Gln |

```
                370             375             380
Lys Lys Phe Cys Phe Pro Val Lys Glu Asn Ile Ser Gln Asp Ile
385                 390             395                 400

Asp His Ile Leu Glu Thr Leu Ser Ala Leu Ala Val Asp Leu Gly Gly
                405             410             415

Thr Asn Leu Arg Val Ala Ile Val Ser Met Lys Gly Glu Ile Val Lys
                420             425             430

Lys Tyr Thr Gln Phe Asn Pro Lys Thr Tyr Glu Glu Arg Ile Asn Leu
            435             440             445

Ile Leu Gln Met Cys Val Glu Ala Ala Glu Ala Val Lys Leu Asn
    450             455             460

Cys Arg Ile Leu Gly Val Gly Ile Ser Thr Gly Arg Val Asn Pro
465             470             475             480

Arg Glu Gly Ile Val Leu His Ser Thr Lys Leu Ile Gln Glu Trp Asn
                485             490             495

Ser Val Asp Leu Arg Thr Pro Leu Ser Asp Thr Leu His Leu Pro Val
                500             505             510

Trp Val Asp Asn Asp Gly Asn Cys Ala Ala Leu Ala Glu Arg Lys Phe
                515             520             525

Gly Gln Gly Lys Gly Leu Glu Asn Phe Val Thr Leu Ile Thr Gly Thr
                530             535             540

Gly Ile Gly Gly Gly Ile Ile His Gln His Glu Leu Ile His Gly Ser
545             550             555             560

Ser Phe Cys Ala Ala Glu Leu Gly His Leu Val Val Ser Leu Asp Gly
                565             570             575

Pro Asp Cys Ser Cys Gly Ser His Gly Cys Ile Glu Ala Tyr Ala Ser
                580             585             590

Gly Met Ala Leu Gln Arg Glu Ala Lys Lys Leu His Asp Glu Asp Leu
                595             600             605

Leu Leu Val Glu Gly Met Ser Val Pro Lys Asp Glu Ala Val Gly Ala
                610             615             620

Leu His Leu Ile Gln Ala Ala Lys Leu Gly Asn Ala Lys Ala Gln Ser
625             630             635             640

Ile Leu Arg Thr Ala Gly Thr Ala Leu Gly Leu Gly Val Val Asn Ile
                645             650             655

Leu His Thr Met Asn Pro Ser Leu Val Ile Leu Ser Gly Val Leu Ala
                660             665             670

Ser His Tyr Ile His Ile Val Lys Asp Val Ile Arg Gln Gln Ala Leu
            675             680             685

Ser Ser Val Gln Asp Val Asp Val Val Ser Asp Leu Val Asp Pro
690             695             700

Ala Leu Leu Gly Ala Ala Ser Met Val Leu Asp Tyr Thr Thr Arg Arg
705             710             715             720

Ile Tyr

<210> SEQ ID NO 4
<211> LENGTH: 400
<212> TYPE: PRT
<213> ORGANISM: Homo sapiens

<400> SEQUENCE: 4

Met Glu Thr Tyr Gly Tyr Leu Gln Arg Glu Ser Cys Phe Gln Gly Pro
1               5                   10                  15

His Glu Leu Tyr Phe Lys Asn Leu Ser Lys Arg Asn Lys Gln Ile Met
```

|  |  |  | 20 |  |  |  | 25 |  |  |  | 30 |  |
|---|---|---|---|---|---|---|---|---|---|---|---|---|

Glu Lys Asn Gly Asn Asn Arg Lys Leu Arg Val Cys Val Ala Thr Cys
     35       40       45

Asn Arg Ala Asp Tyr Ser Lys Leu Ala Pro Ile Met Phe Gly Ile Lys
50       55       60

Thr Glu Pro Glu Phe Phe Glu Leu Asp Val Val Leu Gly Ser His
65       70       75       80

Leu Ile Asp Asp Tyr Gly Asn Thr Tyr Arg Met Ile Glu Gln Asp Asp
       85       90       95

Phe Asp Ile Asn Thr Arg Leu His Thr Ile Val Arg Gly Glu Asp Glu
     100       105       110

Ala Ala Met Val Glu Ser Val Gly Leu Ala Leu Val Lys Leu Pro Asp
     115       120       125

Val Leu Asn Arg Leu Lys Pro Asp Ile Met Ile Val His Gly Asp Arg
   130       135       140

Phe Asp Ala Leu Ala Leu Ala Thr Ser Ala Ala Leu Met Asn Ile Arg
145       150       155       160

Ile Leu His Ile Glu Gly Gly Glu Val Ser Gly Thr Ile Asp Asp Ser
     165       170       175

Ile Arg His Ala Ile Thr Lys Leu Ala His Tyr His Val Cys Cys Thr
     180       185       190

Arg Ser Ala Glu Gln His Leu Ile Ser Met Cys Glu Asp His Asp Arg
     195       200       205

Ile Leu Leu Ala Gly Cys Pro Ser Tyr Asp Lys Leu Leu Ser Ala Lys
   210       215       220

Asn Lys Asp Tyr Met Ser Ile Ile Arg Met Trp Leu Gly Asp Asp Val
225       230       235       240

Lys Ser Lys Asp Tyr Ile Val Ala Leu Gln His Pro Val Thr Thr Asp
     245       250       255

Ile Lys His Ser Ile Lys Met Phe Glu Leu Thr Leu Asp Ala Leu Ile
     260       265       270

Ser Phe Asn Lys Arg Thr Leu Val Leu Phe Pro Asn Ile Asp Ala Gly
   275       280       285

Ser Lys Glu Met Val Arg Val Met Arg Lys Lys Gly Ile Glu His His
   290       295       300

Pro Asn Phe Arg Ala Val Lys His Val Pro Phe Asp Gln Phe Ile Gln
305       310       315       320

Leu Val Ala His Ala Gly Cys Met Ile Gly Asn Ser Ser Cys Gly Val
     325       330       335

Arg Glu Val Gly Ala Phe Gly Thr Pro Val Ile Asn Leu Gly Thr Arg
     340       345       350

Gln Ile Gly Arg Glu Thr Gly Glu Asn Val Leu His Val Arg Asp Ala
   355       360       365

Asp Thr Gln Asp Lys Ile Leu Gln Ala Leu His Leu Gln Phe Gly Lys
   370       375       380

Gln Tyr Pro Cys Ser Lys Ile Tyr Gly Asp Gly Asn Ala Val Pro Arg
385       390       395       400

```
<210> SEQ ID NO 5
<211> LENGTH: 369
<212> TYPE: PRT
<213> ORGANISM: Homo sapiens

<400> SEQUENCE: 5
```

```
Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
        130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
            165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
        210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
            245                 250                 255

Gly Ser Lys Glu Met Val Arg Val Met Arg Lys Lys Gly Ile Glu His
        260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
        290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
            325                 330                 335

Ala Asp Thr Gln Asp Lys Ile Leu Gln Ala Leu His Leu Gln Phe Gly
        340                 345                 350

Lys Gln Tyr Pro Cys Ser Lys Ile Tyr Gly Asp Gly Asn Ala Val Pro
        355                 360                 365

Arg
```

<210> SEQ ID NO 6
<211> LENGTH: 364
<212> TYPE: PRT
<213> ORGANISM: Homo sapiens

<400> SEQUENCE: 6

-continued

Met Pro Ile Gly Asp Cys Ser Val Ala Ala Lys Pro Arg Lys Gln Leu
1               5                   10                  15

Leu Cys Ser Leu Phe Gln Thr Thr Leu Gly Tyr Arg Ala Arg Ala Ser
            20                  25                  30

Gly Trp Lys Pro Met Val Ile Cys Arg Gly Ser His Ala Phe Lys Asp
        35                  40                  45

Leu Ile Asn Thr Tyr Arg Met Ile Glu Gln Asp Asp Phe Asp Ile Asn
    50                  55                  60

Thr Arg Leu His Thr Ile Val Arg Gly Glu Asp Ala Ala Met Val
65                  70                  75                  80

Glu Ser Val Gly Leu Ala Leu Val Lys Leu Pro Asp Val Leu Asn Arg
                85                  90                  95

Leu Lys Pro Asp Ile Met Ile Val His Gly Asp Arg Phe Asp Ala Leu
            100                 105                 110

Ala Leu Ala Thr Ser Ala Ala Leu Met Asn Ile Arg Ile Leu His Ile
            115                 120                 125

Glu Gly Gly Glu Val Ser Gly Thr Ile Asp Asp Ser Ile Arg His Ala
            130                 135                 140

Ile Thr Lys Leu Ala His Tyr His Val Cys Cys Thr Arg Ser Ala Glu
145                 150                 155                 160

Gln His Leu Ile Ser Met Cys Glu Asp His Asp Arg Ile Leu Leu Ala
                165                 170                 175

Gly Cys Pro Ser Tyr Asp Lys Leu Leu Ser Ala Lys Asn Lys Asp Tyr
            180                 185                 190

Met Ser Ile Ile Arg Met Trp Leu Gly Asp Asp Val Lys Ser Lys Asp
            195                 200                 205

Tyr Ile Val Ala Leu Gln His Pro Val Thr Thr Asp Ile Lys His Ser
210                 215                 220

Ile Lys Met Phe Glu Leu Thr Leu Asp Ala Leu Ile Ser Phe Asn Lys
225                 230                 235                 240

Arg Thr Leu Val Leu Phe Pro Asn Ile Asp Ala Gly Ser Lys Glu Met
                245                 250                 255

Val Arg Val Met Arg Lys Lys Gly Ile Glu His His Pro Asn Phe Arg
            260                 265                 270

Ala Val Lys His Val Pro Phe Asp Gln Phe Ile Gln Leu Val Ala His
            275                 280                 285

Ala Gly Cys Met Ile Gly Asn Ser Ser Cys Gly Val Arg Glu Val Gly
            290                 295                 300

Ala Phe Gly Thr Pro Val Ile Asn Leu Gly Thr Arg Gln Ile Gly Arg
305                 310                 315                 320

Glu Thr Gly Glu Asn Val Leu His Val Arg Asp Ala Asp Thr Gln Asp
                325                 330                 335

Lys Ile Leu Gln Ala Leu His Leu Gln Phe Gly Lys Gln Tyr Pro Cys
            340                 345                 350

Ser Lys Ile Tyr Gly Asp Gly Asn Ala Val Pro Arg
            355                 360

<210> SEQ ID NO 7
<211> LENGTH: 293
<212> TYPE: PRT
<213> ORGANISM: Homo sapiens

<400> SEQUENCE: 7

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Asn Pro Ile Leu His Ile Glu Gly Gly Glu Val Ser Gly Thr Ile
130                 135                 140

Asp Asp Ser Ile Arg His Ala Ile Thr Lys Leu Ala His Tyr His Val
145                 150                 155                 160

Cys Cys Thr Arg Ser Ala Glu Gln His Leu Ile Ser Met Cys Glu Asp
                165                 170                 175

His Asp Arg Ile Leu Leu Ala Gly Cys Pro Ser Tyr Asp Lys Leu Leu
            180                 185                 190

Ser Ala Lys Asn Lys Asp Tyr Met Ser Ile Ile Arg Met Trp Leu Gly
        195                 200                 205

Asp Asp Val Asn Pro Lys Ser Lys Asp Tyr Ile Val Ala Leu Gln His
210                 215                 220

Pro Val Thr Thr Asp Ile Lys His Ser Ile Lys Met Phe Glu Leu Thr
225                 230                 235                 240

Leu Asp Ala Leu Ile Ser Phe Asn Lys Arg Thr Leu Val Leu Phe Pro
                245                 250                 255

Asn Ile Asp Ala Gly Ser Lys Glu Met Val Arg Val Met Arg Lys Lys
            260                 265                 270

Gly Ile Glu His His Pro Asn Phe Arg Ala Val Lys His Val Pro Phe
        275                 280                 285

Asp Gln Phe Ile Gln
    290

<210> SEQ ID NO 8
<211> LENGTH: 179
<212> TYPE: PRT
<213> ORGANISM: Homo sapiens

<400> SEQUENCE: 8

Met Ile Glu Gln Asp Asp Phe Asp Ile Asn Thr Arg Leu His Thr Ile
1               5                   10                  15

Val Arg Gly Glu Asp Glu Ala Ala Met Val Glu Ser Val Gly Leu Ala
            20                  25                  30

Leu Val Lys Leu Pro Asp Val Leu Asn Arg Leu Lys Pro Asp Ile Met
        35                  40                  45

Ile Val His Gly Asp Arg Phe Asp Ala Leu Ala Leu Ala Thr Ser Ala
    50                  55                  60

Ala Leu Met Asn Ile Arg Ile Leu His Ile Glu Gly Gly Glu Val Ser
65                  70                  75                  80

Gly Thr Ile Asp Asp Ser Ile Arg His Ala Ile Thr Lys Leu Ala His

```
                    85                  90                  95
Tyr His Val Cys Cys Thr Arg Ser Ala Glu Gln His Leu Ile Ser Met
                100                 105                 110
Cys Glu Asp His Asp Arg Ile Leu Leu Ala Gly Cys Pro Ser Tyr Asp
            115                 120                 125
Lys Leu Leu Ser Ala Lys Asn Lys Asp Tyr Met Ser Ile Ile Arg Met
        130                 135                 140
Trp Leu Gly Ser Lys Glu Met Val Arg Val Met Arg Lys Lys Gly Ile
145                 150                 155                 160
Glu His His Pro Asn Phe Arg Ala Val Lys His Val Pro Phe Asp Gln
                165                 170                 175
Phe Ile Gln

<210> SEQ ID NO 9
<211> LENGTH: 31
<212> TYPE: PRT
<213> ORGANISM: Homo sapiens

<400> SEQUENCE: 9

Thr Leu Val Leu Phe Pro Asn Ile Asp Ala Gly Ser Lys Glu Met Val
1               5                   10                  15
Arg Val Met Arg Lys Lys Gly Ile Glu His His Pro Asn Phe Arg
            20                  25                  30

<210> SEQ ID NO 10
<211> LENGTH: 31
<212> TYPE: PRT
<213> ORGANISM: Homo sapiens

<400> SEQUENCE: 10

Thr Leu Val Leu Phe Pro Asn Ile Asp Ala Gly Ser Lys Glu Met Val
1               5                   10                  15
Gln Val Met Arg Lys Lys Gly Ile Glu His His Pro Asn Phe Arg
            20                  25                  30

<210> SEQ ID NO 11
<211> LENGTH: 31
<212> TYPE: PRT
<213> ORGANISM: Homo sapiens

<400> SEQUENCE: 11

Thr Leu Val Leu Phe Pro Asn Ile Asp Ala Gly Ser Lys Glu Met Val
1               5                   10                  15
Trp Val Met Arg Lys Lys Gly Ile Glu His His Pro Asn Phe Arg
            20                  25                  30

<210> SEQ ID NO 12
<211> LENGTH: 31
<212> TYPE: PRT
<213> ORGANISM: Homo sapiens

<400> SEQUENCE: 12

Thr Leu Val Leu Phe Pro Asn Ile Asp Ala Gly Ser Lys Glu Met Val
1               5                   10                  15
Leu Val Met Arg Lys Lys Gly Ile Glu His His Pro Asn Phe Arg
            20                  25                  30

<210> SEQ ID NO 13
<211> LENGTH: 31
<212> TYPE: PRT
```

<213> ORGANISM: Homo sapiens

<400> SEQUENCE: 13

Thr Leu Val Leu Phe Pro Asn Ile Asp Ala Gly Ser Lys Glu Met Val
1               5                   10                  15

Arg Val Met Gln Lys Lys Gly Ile Glu His His Pro Asn Phe Arg
            20                  25                  30

<210> SEQ ID NO 14
<211> LENGTH: 31
<212> TYPE: PRT
<213> ORGANISM: Homo sapiens

<400> SEQUENCE: 14

Thr Leu Val Leu Phe Pro Asn Ile Asp Ala Gly Ser Lys Glu Met Val
1               5                   10                  15

Arg Val Met Trp Lys Lys Gly Ile Glu His His Pro Asn Phe Arg
            20                  25                  30

<210> SEQ ID NO 15
<211> LENGTH: 753
<212> TYPE: PRT
<213> ORGANISM: Homo sapiens
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid

<400> SEQUENCE: 15

Met Glu Thr Tyr Gly Tyr Leu Gln Arg Glu Ser Cys Phe Gln Gly Pro
1               5                   10                  15

His Glu Leu Tyr Phe Lys Asn Leu Ser Lys Arg Asn Lys Gln Ile Met
            20                  25                  30

Glu Lys Asn Gly Asn Asn Arg Lys Leu Arg Val Cys Val Ala Thr Cys
        35                  40                  45

Asn Arg Ala Asp Tyr Ser Lys Leu Ala Pro Ile Met Phe Gly Ile Lys
    50                  55                  60

Thr Glu Pro Glu Phe Phe Glu Leu Asp Val Val Val Leu Gly Ser His
65                  70                  75                  80

Leu Ile Asp Asp Tyr Gly Asn Thr Tyr Arg Met Ile Glu Gln Asp Asp
                85                  90                  95

Phe Asp Ile Asn Thr Arg Leu His Thr Ile Val Arg Gly Glu Asp Glu
            100                 105                 110

Ala Ala Met Val Glu Ser Val Gly Leu Ala Leu Val Lys Leu Pro Asp
        115                 120                 125

Val Leu Asn Arg Leu Lys Pro Asp Ile Met Ile Val His Gly Asp Arg
    130                 135                 140

Phe Asp Ala Leu Ala Leu Ala Thr Ser Ala Ala Leu Met Asn Ile Arg
145                 150                 155                 160

Ile Leu His Ile Glu Gly Gly Glu Val Ser Gly Thr Ile Asp Asp Ser
                165                 170                 175

Ile Arg His Ala Ile Thr Lys Leu Ala His Tyr His Val Cys Cys Thr
            180                 185                 190

Arg Ser Ala Glu Gln His Leu Ile Ser Met Cys Glu Asp His Asp Arg
        195                 200                 205

```
Ile Leu Leu Ala Gly Cys Pro Ser Tyr Asp Lys Leu Leu Ser Ala Lys
210                 215                 220

Asn Lys Asp Tyr Met Ser Ile Ile Arg Met Trp Leu Gly Asp Asp Val
225                 230                 235                 240

Lys Ser Lys Asp Tyr Ile Val Ala Leu Gln His Pro Val Thr Thr Asp
                245                 250                 255

Ile Lys His Ser Ile Lys Met Phe Glu Leu Thr Leu Asp Ala Leu Ile
            260                 265                 270

Ser Phe Asn Lys Arg Thr Leu Val Leu Phe Pro Asn Ile Asp Ala Gly
        275                 280                 285

Ser Lys Glu Met Val Xaa Val Met Xaa Lys Lys Gly Ile Glu His His
290                 295                 300

Pro Asn Phe Arg Ala Val Lys His Val Pro Phe Asp Gln Phe Ile Gln
305                 310                 315                 320

Leu Val Ala His Ala Gly Cys Met Ile Gly Asn Ser Ser Cys Gly Val
                325                 330                 335

Arg Glu Val Gly Ala Phe Gly Thr Pro Val Ile Asn Leu Gly Thr Arg
            340                 345                 350

Gln Ile Gly Arg Glu Thr Gly Glu Asn Val Leu His Val Arg Asp Ala
        355                 360                 365

Asp Thr Gln Asp Lys Ile Leu Gln Ala Leu His Leu Gln Phe Gly Lys
370                 375                 380

Gln Tyr Pro Cys Ser Lys Ile Tyr Gly Asp Gly Asn Ala Val Pro Arg
385                 390                 395                 400

Ile Leu Lys Phe Leu Lys Ser Ile Asp Leu Gln Glu Pro Leu Gln Lys
                405                 410                 415

Lys Phe Cys Phe Pro Pro Val Lys Glu Asn Ile Ser Gln Asp Ile Asp
            420                 425                 430

His Ile Leu Glu Thr Leu Ser Ala Leu Ala Val Asp Leu Gly Gly Thr
        435                 440                 445

Asn Leu Arg Val Ala Ile Val Ser Met Lys Gly Glu Ile Val Lys Lys
450                 455                 460

Tyr Thr Gln Phe Asn Pro Lys Thr Tyr Glu Glu Arg Ile Asn Leu Ile
465                 470                 475                 480

Leu Gln Met Cys Val Glu Ala Ala Glu Ala Val Lys Leu Asn Cys
                485                 490                 495

Arg Ile Leu Gly Val Gly Ile Ser Thr Gly Gly Arg Val Asn Pro Arg
            500                 505                 510

Glu Gly Ile Val Leu His Ser Thr Lys Leu Ile Gln Glu Trp Asn Ser
        515                 520                 525

Val Asp Leu Arg Thr Pro Leu Ser Asp Thr Leu His Leu Pro Val Trp
530                 535                 540

Val Asp Asn Asp Gly Asn Cys Ala Ala Leu Ala Glu Arg Lys Phe Gly
545                 550                 555                 560

Gln Gly Lys Gly Leu Glu Asn Phe Val Thr Leu Ile Thr Gly Thr Gly
                565                 570                 575

Ile Gly Gly Gly Ile Ile His Gln His Glu Leu Ile His Gly Ser Ser
            580                 585                 590

Phe Cys Ala Ala Glu Leu Gly His Leu Val Val Ser Leu Asp Gly Pro
        595                 600                 605

Asp Cys Ser Cys Gly Ser His Gly Cys Ile Glu Ala Tyr Ala Ser Gly
610                 615                 620

Met Ala Leu Gln Arg Glu Ala Lys Lys Leu His Asp Glu Asp Leu Leu
```

```
                625                 630                 635                 640
Leu Val Glu Gly Met Ser Val Pro Lys Asp Glu Ala Val Gly Ala Leu
                    645                 650                 655
His Leu Ile Gln Ala Ala Lys Leu Gly Asn Ala Lys Ala Gln Ser Ile
                660                 665                 670
Leu Arg Thr Ala Gly Thr Ala Leu Gly Leu Gly Val Val Asn Ile Leu
            675                 680                 685
His Thr Met Asn Pro Ser Leu Val Ile Leu Ser Gly Val Leu Ala Ser
690                 695                 700
His Tyr Ile His Ile Val Lys Asp Val Ile Arg Gln Gln Ala Leu Ser
705                 710                 715                 720
Ser Val Gln Asp Val Asp Val Val Ser Asp Leu Val Asp Pro Ala
                725                 730                 735
Leu Leu Gly Ala Ala Ser Met Val Leu Asp Tyr Thr Thr Arg Arg Ile
            740                 745                 750
Tyr

<210> SEQ ID NO 16
<211> LENGTH: 648
<212> TYPE: PRT
<213> ORGANISM: Homo sapiens
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid

<400> SEQUENCE: 16

Met Glu Lys Asn Gly Asn Asn Arg Lys Leu Arg Val Cys Val Ala Thr
1               5                   10                  15
Cys Asn Arg Ala Asp Tyr Ser Lys Leu Ala Pro Ile Met Phe Gly Ile
            20                  25                  30
Lys Thr Glu Pro Glu Phe Phe Glu Leu Asp Val Val Val Leu Gly Ser
        35                  40                  45
His Leu Ile Asp Asp Tyr Gly Asn Thr Tyr Arg Met Ile Glu Gln Asp
    50                  55                  60
Asp Phe Asp Ile Asn Thr Arg Leu His Thr Ile Val Arg Gly Glu Asp
65                  70                  75                  80
Glu Ala Ala Met Val Glu Ser Val Gly Leu Ala Leu Val Lys Leu Pro
                85                  90                  95
Asp Val Leu Asn Arg Leu Lys Pro Asp Ile Met Ile Val His Gly Asp
            100                 105                 110
Arg Phe Asp Ala Leu Ala Leu Ala Thr Ser Ala Ala Leu Met Asn Ile
        115                 120                 125
Arg Ile Leu His Ile Glu Gly Gly Glu Val Ser Gly Thr Ile Asp Asp
    130                 135                 140
Ser Ile Arg His Ala Ile Thr Lys Leu Ala His Tyr His Val Cys Cys
145                 150                 155                 160
Thr Arg Ser Ala Glu Gln His Leu Ile Ser Met Cys Glu Asp His Asp
                165                 170                 175
Arg Ile Leu Leu Ala Gly Cys Pro Ser Tyr Asp Lys Leu Leu Ser Ala
            180                 185                 190
Lys Asn Lys Asp Tyr Met Ser Ile Ile Arg Met Trp Leu Gly Asp Asp
        195                 200                 205
```

Val Lys Ser Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Xaa Val Met Xaa Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
        435                 440                 445

Ile Leu Gln Met Cys Val Glu Ala Ala Glu Ala Val Lys Leu Asn
    450                 455                 460

Cys Arg Ile Leu Gly Val Gly Ile Gly Gly Ile Ile His Gln His
465                 470                 475                 480

Glu Leu Ile His Gly Ser Ser Phe Cys Ala Ala Glu Leu Gly His Leu
                485                 490                 495

Val Val Ser Leu Asp Gly Pro Asp Cys Ser Cys Gly Ser His Gly Cys
            500                 505                 510

Ile Glu Ala Tyr Ala Ser Gly Met Ala Leu Gln Arg Glu Ala Lys Lys
        515                 520                 525

Leu His Asp Glu Asp Leu Leu Leu Val Glu Gly Met Ser Val Pro Lys
    530                 535                 540

Asp Glu Ala Val Gly Ala Leu His Leu Ile Gln Ala Ala Lys Leu Gly
545                 550                 555                 560

Asn Ala Lys Ala Gln Ser Ile Leu Arg Thr Ala Gly Thr Ala Leu Gly
                565                 570                 575

Leu Gly Val Val Asn Ile Leu His Thr Met Asn Pro Ser Leu Val Ile
            580                 585                 590

Leu Ser Gly Val Leu Ala Ser His Tyr Ile His Ile Val Lys Asp Val
        595                 600                 605

Ile Arg Gln Gln Ala Leu Ser Ser Val Gln Asp Val Asp Val Val Val
    610                 615                 620

```
Ser Asp Leu Val Asp Pro Ala Leu Leu Gly Ala Ala Ser Met Val Leu
625                 630                 635                 640

Asp Tyr Thr Thr Arg Arg Ile Tyr
                645

<210> SEQ ID NO 17
<211> LENGTH: 612
<212> TYPE: PRT
<213> ORGANISM: Homo sapiens
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid

<400> SEQUENCE: 17

Met Ile Glu Gln Asp Asp Phe Asp Ile Asn Thr Arg Leu His Thr Ile
1               5                   10                  15

Val Arg Gly Glu Asp Glu Ala Ala Met Val Glu Ser Val Gly Leu Ala
            20                  25                  30

Leu Val Lys Leu Pro Asp Val Leu Asn Arg Leu Lys Pro Asp Ile Met
        35                  40                  45

Ile Val His Gly Asp Arg Phe Asp Ala Leu Ala Leu Ala Thr Ser Ala
    50                  55                  60

Ala Leu Met Asn Ile Arg Ile Leu His Ile Glu Gly Gly Glu Val Ser
65                  70                  75                  80

Gly Thr Ile Asp Asp Ser Ile Arg His Ala Ile Thr Lys Leu Ala His
                85                  90                  95

Tyr His Val Cys Cys Thr Arg Ser Ala Glu Gln His Leu Ile Ser Met
            100                 105                 110

Cys Glu Asp His Asp Arg Ile Leu Leu Ala Gly Cys Pro Ser Tyr Asp
        115                 120                 125

Lys Leu Leu Ser Ala Lys Asn Lys Asp Tyr Met Ser Ile Ile Arg Met
    130                 135                 140

Trp Leu Gly Ser Lys Glu Met Val Xaa Val Met Xaa Lys Lys Gly Ile
145                 150                 155                 160

Glu His His Pro Asn Phe Arg Ala Val Lys His Val Pro Phe Asp Gln
                165                 170                 175

Phe Ile Gln Leu Val Ala His Ala Gly Cys Met Ile Gly Asn Ser Ser
            180                 185                 190

Cys Gly Val Arg Glu Val Gly Ala Phe Gly Thr Pro Val Ile Asn Leu
        195                 200                 205

Gly Thr Arg Gln Ile Gly Arg Glu Thr Gly Glu Asn Val Leu His Val
    210                 215                 220

Arg Asp Ala Asp Thr Gln Asp Lys Ile Leu Gln Ala Leu His Leu Gln
225                 230                 235                 240

Phe Gly Lys Gln Tyr Pro Cys Ser Lys Ile Tyr Gly Asp Gly Asn Ala
                245                 250                 255

Val Pro Arg Ile Leu Lys Phe Leu Lys Ser Ile Asp Leu Gln Glu Pro
            260                 265                 270

Leu Gln Lys Lys Phe Cys Phe Pro Pro Val Lys Glu Asn Ile Ser Gln
        275                 280                 285

Asp Ile Asp His Ile Leu Glu Thr Leu Ser Ala Leu Ala Val Asp Leu
    290                 295                 300
```

-continued

```
Gly Gly Thr Asn Leu Arg Val Ala Ile Val Ser Met Lys Gly Glu Ile
305                 310                 315                 320

Val Lys Lys Tyr Thr Gln Phe Asn Pro Lys Thr Tyr Glu Glu Arg Ile
            325                 330                 335

Asn Leu Ile Leu Gln Met Cys Val Glu Ala Ala Glu Ala Val Lys
            340                 345                 350

Leu Asn Cys Arg Ile Leu Gly Val Gly Ile Ser Thr Gly Gly Arg Val
355                 360                 365

Asn Pro Arg Glu Gly Ile Val Leu His Ser Thr Lys Leu Ile Gln Glu
        370                 375                 380

Trp Asn Ser Val Asp Leu Arg Thr Pro Leu Ser Asp Thr Leu His Leu
385                 390                 395                 400

Pro Val Trp Val Asp Asn Asp Gly Asn Cys Ala Ala Leu Ala Glu Arg
                405                 410                 415

Lys Phe Gly Gln Gly Lys Gly Leu Glu Asn Phe Val Thr Leu Ile Thr
            420                 425                 430

Gly Thr Gly Ile Gly Gly Ile Ile His Gln His Glu Leu Ile His
        435                 440                 445

Gly Ser Ser Phe Cys Ala Ala Glu Leu Gly His Leu Val Val Ser Leu
450                 455                 460

Asp Gly Pro Asp Cys Ser Cys Gly Ser His Gly Cys Ile Glu Ala Tyr
465                 470                 475                 480

Ala Ser Gly Met Ala Leu Gln Arg Glu Ala Lys Lys Leu His Asp Glu
                485                 490                 495

Asp Leu Leu Leu Val Glu Gly Met Ser Val Pro Lys Asp Glu Ala Val
            500                 505                 510

Gly Ala Leu His Leu Ile Gln Ala Ala Lys Leu Gly Asn Ala Lys Ala
        515                 520                 525

Gln Ser Ile Leu Arg Thr Ala Gly Thr Ala Leu Gly Leu Gly Val Val
530                 535                 540

Asn Ile Leu His Thr Met Asn Pro Ser Leu Val Ile Leu Ser Gly Val
545                 550                 555                 560

Leu Ala Ser His Tyr Ile His Ile Val Lys Asp Val Ile Arg Gln Gln
                565                 570                 575

Ala Leu Ser Ser Val Gln Asp Val Asp Val Val Ser Asp Leu Val
            580                 585                 590

Asp Pro Ala Leu Leu Gly Ala Ala Ser Met Val Leu Asp Tyr Thr Thr
        595                 600                 605

Arg Arg Ile Tyr
    610

<210> SEQ ID NO 18
<211> LENGTH: 466
<212> TYPE: PRT
<213> ORGANISM: Homo sapiens

<400> SEQUENCE: 18

Asp Asn Ala Tyr Phe Gly Tyr Ser Thr Pro Trp Gly Tyr Phe Asp Phe
1               5                   10                  15

Asn Arg Phe His Cys His Phe Ser Pro Arg Asp Trp Gln Arg Leu Ile
            20                  25                  30

Asn Asn Asn Trp Gly Phe Arg Pro Lys Arg Leu Asn Phe Lys Leu Phe
        35                  40                  45

Asn Ile Gln Val Lys Glu Val Thr Asp Asn Asn Gly Val Lys Thr Ile
50                  55                  60
```

```
Ala Asn Asn Leu Thr Ser Thr Val Gln Val Phe Thr Asp Ser Asp Tyr
 65                  70                  75                  80

Gln Leu Pro Tyr Val Leu Gly Ser Ala His Glu Gly Cys Leu Pro Pro
                 85                  90                  95

Phe Pro Ala Asp Val Phe Met Ile Pro Gln Tyr Gly Tyr Leu Thr Leu
            100                 105                 110

Asn Asp Gly Ser Gln Ala Val Gly Arg Ser Ser Phe Tyr Cys Leu Glu
            115                 120                 125

Tyr Phe Pro Ser Gln Met Leu Arg Thr Gly Asn Asn Phe Gln Phe Ser
            130                 135                 140

Tyr Glu Phe Glu Asn Val Pro Phe His Ser Ser Tyr Ala His Ser Gln
145                 150                 155                 160

Ser Leu Asp Arg Leu Met Asn Pro Leu Ile Asp Gln Tyr Leu Tyr Tyr
                165                 170                 175

Leu Ser Lys Thr Ile Asn Gly Ser Gly Gln Asn Gln Gln Thr Leu Lys
            180                 185                 190

Phe Ser Val Ala Gly Pro Ser Asn Met Ala Val Gln Gly Arg Asn Tyr
            195                 200                 205

Ile Pro Gly Pro Ser Tyr Arg Gln Gln Arg Val Ser Thr Thr Val Thr
210                 215                 220

Gln Asn Asn Asn Ser Glu Phe Ala Trp Asp Asn Ala Tyr Phe Gly Tyr
225                 230                 235                 240

Ser Thr Pro Trp Gly Tyr Phe Asp Phe Asn Arg Phe His Cys His Phe
                245                 250                 255

Ser Pro Arg Asp Trp Gln Arg Leu Ile Asn Asn Asn Trp Gly Phe Arg
            260                 265                 270

Pro Lys Arg Leu Asn Phe Lys Leu Phe Asn Ile Gln Val Lys Glu Val
            275                 280                 285

Thr Asp Asn Asn Gly Val Lys Thr Ile Ala Asn Asn Leu Thr Ser Thr
            290                 295                 300

Val Gln Val Phe Thr Asp Ser Asp Tyr Gln Leu Pro Tyr Val Leu Gly
305                 310                 315                 320

Ser Ala His Glu Gly Cys Leu Pro Pro Phe Pro Ala Asp Val Phe Met
                325                 330                 335

Ile Pro Gln Tyr Gly Tyr Leu Thr Leu Asn Asp Gly Ser Gln Ala Val
            340                 345                 350

Gly Arg Ser Ser Phe Tyr Cys Leu Glu Tyr Phe Pro Ser Gln Met Leu
            355                 360                 365

Arg Thr Gly Asn Asn Phe Gln Phe Ser Tyr Glu Phe Glu Asn Val Pro
            370                 375                 380

Phe His Ser Ser Tyr Ala His Ser Gln Ser Leu Asp Arg Leu Met Asn
385                 390                 395                 400

Pro Leu Ile Asp Gln Tyr Leu Tyr Tyr Leu Ser Lys Thr Ile Asn Gly
                405                 410                 415

Ser Gly Gln Asn Gln Gln Thr Leu Lys Phe Ser Val Ala Gly Pro Ser
            420                 425                 430

Asn Met Ala Val Gln Gly Arg Asn Tyr Ile Pro Gly Pro Ser Tyr Arg
            435                 440                 445

Gln Gln Arg Val Ser Thr Thr Val Thr Gln Asn Asn Asn Ser Glu Phe
            450                 455                 460

Ala Trp
465
```

<210> SEQ ID NO 19
<211> LENGTH: 233
<212> TYPE: PRT
<213> ORGANISM: Homo sapiens
<220> FEATURE:
<221> NAME/KEY: misc_feature
<222> LOCATION: (3)..(175)
<223> OTHER INFORMATION: Xaa can be any naturally occurring amino acid
<220> FEATURE:
<221> NAME/KEY: misc_feature
<222> LOCATION: (177)..(199)
<223> OTHER INFORMATION: Xaa can be any naturally occurring amino acid
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (204)..(232)
<223> OTHER INFORMATION: Xaa can be any naturally occurring amino acid

<400> SEQUENCE: 19

```
Asp Asn Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Tyr
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Asn Xaa Ala Val Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Trp
225                 230
```

What is claimed is:

1. A method of treating GNE myopathy in a subject, the method comprising administering to the subject a pharmaceutical composition comprising a recombinant Adeno-associated virus (AAV) vector comprising a DNA molecule encoding GNE or a therapeutic fragment thereof,
   wherein the recombinant AAV vector has a capsid comprising amino acid residues corresponding to Asp-271, Asn-272, Tyr-446, Asn-470, and Trp-503 as described in SEQ ID NO: 18 and 19 as Asp-1 or 234, Asn-2 or 235, Tyr-176 or 409, Asn-200 or 433, and Trp-233 or 466, thereby directing entry of the AAV vector into cells of the subject without a need for sialic acid on the cells, and
   wherein the GNE or a therapeutic fragment thereof comprises at least one mutation or variation within an allosteric domain of GNE.

2. The method of claim 1, wherein the pharmaceutical composition has a net negative charge.

3. The method of claim 1, wherein the pharmaceutical composition is administered intravenously.

4. The method of claim 1, further comprising at least one eukaryotic enhancer.

5. The method of claim 1, wherein subsequent to the administration of the pharmaceutical composition, the subject experiences an increase in sialic content.

6. The method of claim 1, wherein the subject has at least one mutation in the gene encoding GNE.

7. The method of claim 1, comprising administering the pharmaceutical composition to a limb or limbs of the subject.

8. The method of claim 1, wherein subsequent to the administration of the pharmaceutical composition, the subject experiences an improvement in sialylation.

9. The method of claim 1, wherein subsequent to the administration of the pharmaceutical composition, the subject experiences an improvement in muscle function.

10. The method of claim 1, wherein the pharmaceutical composition is administered by hydrodynamic infusion.

11. A pharmaceutical composition comprising a recombinant Adeno-associated virus (AAV) vector comprising a DNA molecule encoding GNE or a therapeutic fragment thereof,
    wherein the recombinant AAV vector has a capsid comprising amino acid residues corresponding to Asp-271, Asn-272, Tyr-446, Asn-470, and Trp-503 as described in SEQ ID NO: 18 and 19 as Asp-1 or 234, Asn-2 or 235, Tyr-176 or 409, Asn-200 or 433, and Trp-233 or 466, thereby directing entry of the AAV vector into cells of the subject by forming a molecular pocket comprising required amino acid residues for binding to galactose on the cells, and
    wherein the GNE or a therapeutic fragment thereof comprises at least one mutation or variation within an allosteric domain of GNE.

12. The pharmaceutical composition of claim 11, wherein the pharmaceutical composition has a net negative charge.

13. The pharmaceutical composition of claim 11, further comprising at least one gene therapy vector comprising at least one DNA molecule described by SEQ ID NO: 1 or 2.

14. A pharmaceutical composition comprising at least one DNA molecule described by SEQ ID NO: 1 or 2.

15. The pharmaceutical composition of claim 14, wherein the pharmaceutical composition has a net negative charge.

16. The pharmaceutical composition of claim 14, further comprising at least one pharmaceutically-acceptable carrier, adjuvant, or vehicle.

17. The pharmaceutical composition of claim 14, further comprising at least one AAV vector comprising at least one DNA molecule encoding GNE or a therapeutic fragment thereof.

* * * * *